(12) United States Patent
Okuno et al.

(10) Patent No.: US 8,949,157 B2
(45) Date of Patent: Feb. 3, 2015

(54) ESTIMATION OF PROTEIN-COMPOUND INTERACTION AND RATIONAL DESIGN OF COMPOUND LIBRARY BASED ON CHEMICAL GENOMIC INFORMATION

(75) Inventors: Yasushi Okuno, Kyoto (JP); Kei Taneishi, Kyoto (JP); Gozoh Tsujimoto, Kyoto (JP)

(73) Assignee: Kyoto University, Kyoto (JP)

( * ) Notice: Subject to any disclaimer, the term of this patent is extended or adjusted under 35 U.S.C. 154(b) by 1117 days.

(21) Appl. No.: 12/274,744

(22) Filed: Nov. 20, 2008

(65) Prior Publication Data

US 2010/0099891 A1    Apr. 22, 2010

Related U.S. Application Data

(63) Continuation-in-part of application No. PCT/JP2007/060736, filed on May 25, 2007.

(30) Foreign Application Priority Data

May 26, 2006   (JP) ................................. 2006-147433

(51) Int. Cl.
*G06F 15/18* (2006.01)
*C40B 50/02* (2006.01)
(Continued)

(52) U.S. Cl.
CPC ................ *C40B 50/02* (2013.01); *G06F 19/24* (2013.01); *G06F 19/706* (2013.01); *G06F 19/16* (2013.01)
USPC .......................................................... 706/12

(58) Field of Classification Search
CPC ............................... G06F 19/24; G06F 19/707
USPC ............ 435/4; 702/19–32; 706/12–13, 45–46
See application file for complete search history.

(56) References Cited

U.S. PATENT DOCUMENTS 6,188,965 B1 *   2/2001   Mayo et al. ..................... 702/27
6,349,265 B1 *   2/2002   Pitman et al. ................... 702/27
(Continued)

FOREIGN PATENT DOCUMENTS

WO     0025106       5/2000
WO     0169440 A1    9/2001

OTHER PUBLICATIONS

Lo, Siaw Ling et al.; "Effect of training datasets on support vector machine prediction of protein-protein interactions"; 2005; Wiley-VCH Verlag GmbH & Co.; Proteomics 2005, 5; pp. 876-884.*
(Continued)

*Primary Examiner* — Stanley K Hill
(74) *Attorney, Agent, or Firm* — Studebaker & Brackett PC

(57) ABSTRACT

A data processing method for an estimation of compound-protein interaction using both chemical substance information, such as a chemical property of the compound, and biological information, such as sequence information of genes to rationally and efficiently screen compounds. First space representing space coordinates of a first chemical substance group and second space representing space coordinates of a second chemical substance group are defined, and the first chemical substance group is characterized by a first characteristic amount and the second chemical substance group is characterized by a second characteristic amount, and map transformation of the coordinates of the first space and the coordinates of the second space results in the solution so as to increase the correlation between the first space and the second space using a multivariable analysis technique or a machine learning method.

4 Claims, 14 Drawing Sheets

(51) Int. Cl.
*G06F 19/24* (2011.01)
*G06F 19/00* (2011.01)
*G06F 19/16* (2011.01)

(56) References Cited

U.S. PATENT DOCUMENTS

| | | | |
|---|---|---|---|
| 6,599,694 B2* | 7/2003 | Elias | 435/4 |
| 6,651,008 B1* | 11/2003 | Vaisberg et al. | 435/4 |
| 6,743,576 B1* | 6/2004 | Sabry et al. | 435/4 |
| 7,679,740 B2* | 3/2010 | Neiss et al. | 356/301 |
| 7,894,995 B2* | 2/2011 | Jojic et al. | 702/19 |
| 8,185,321 B2* | 5/2012 | Sakakibara et al. | 702/19 |
| 2002/0090631 A1* | 7/2002 | Gough et al. | 435/6 |
| 2002/0119441 A1* | 8/2002 | Elias | 435/4 |
| 2002/0187514 A1* | 12/2002 | Chen et al. | 435/7.1 |
| 2003/0162224 A1* | 8/2003 | Chait et al. | 435/7.1 |
| 2003/0187587 A1* | 10/2003 | Swindells et al. | 702/19 |
| 2003/0228565 A1* | 12/2003 | Oestreicher et al. | 435/4 |
| 2004/0073527 A1* | 4/2004 | Sherr | 706/20 |
| 2005/0053999 A1* | 3/2005 | Gough et al. | 435/6 |
| 2005/0137806 A1* | 6/2005 | Kutsyy et al. | 702/19 |
| 2006/0036371 A1* | 2/2006 | Gough et al. | 702/19 |
| 2006/0064415 A1* | 3/2006 | Guyon et al. | 707/6 |
| 2006/0106544 A1* | 5/2006 | Ohta et al. | 702/19 |
| 2007/0294068 A1* | 12/2007 | Jones et al. | 703/11 |
| 2009/0259607 A1* | 10/2009 | Fukunishi et al. | 706/20 |
| 2009/0312190 A1* | 12/2009 | Chinea Santiago et al. | 506/8 |

OTHER PUBLICATIONS

Bock, Joel R. et al.; "Predicting protein-protein interactions from primary structure"; 2001; Oxford University Press; Bioinformatics, vol. 17 No. 5; pp. 455-460.*

Gomez, Shawn M. et al.; "Learning to predict protein-protein interactions from protein sequences"; 2003; Oxford University Press 2003; Bioinformatics, vol. 19 No. 15; pp. 1875-1881.*

Guo, Yanzhi et al.; "Using support vector machine combined with auto covariance to predict protein-protein interactions from protein sequences"; Apr. 2008; Published online; Nucleic Acids Research, 2008, vol. 36, No. 9; pp. 3025-3030.*

Kazuyuki Shimizu, "The Mathematics for Life Analysis", Corona Publishing Co., Ltd., Jun. 30, 1999, pp. 117-130.

* cited by examiner

FIG. 11

Library example: Bioactivity annotation of PubChem compounds G.O. Function

| | score 27 | score 26 | score 25 | score 24 | score 23 | score 22 | score 21 |
|---|---|---|---|---|---|---|---|
| motor activity | 0 | 0 | 0 | 12859 | 58294 | 145521 | 30441 |
| catalytic activity | 0 | 132 | 7498 | 91872 | 808264 | 2220698 | 805438 |
| helicase activity | 0 | 0 | 0 | 12763 | 67267 | 197040 | 44202 |
| signal transducer activity | 198 | 94476 | 633290 | 1512369 | 2068061 | 2517613 | 474165 |
| receptor activity | 198 | 99111 | 677597 | 1623305 | 2387872 | 3033699 | 726701 |
| structural molecule activity | 0 | 119 | 3285 | 24141 | 233610 | 587076 | 147335 |
| transporter activity | 0 | 17186 | 424389 | 1075678 | 1577678 | 2119350 | 468872 |
| carrier activity | 0 | 12916 | 325688 | 804791 | 1032175 | 1335641 | 223948 |
| binding | 77 | 52722 | 490419 | 1599411 | 3075508 | 3886455 | 2047957 |
| electron transporter activity | 0 | 128 | 310 | 18706 | 348653 | 904792 | 220589 |
| protein binding | 0 | 28167 | 505062 | 1217307 | 1779455 | 2617458 | 752057 |
| molecular_function unknown | 0 | 0 | 1 | 25707 | 74223 | 275611 | 49685 |
| aromatase activity | 0 | 0 | 0 | 123 | 7033 | 39455 | 6987 |
| protein transporter activity | 0 | 0 | 0 | 333 | 79719 | 77269 | 9330 |
| integrase activity | 0 | 119 | 2565 | 11430 | 45211 | 193815 | 42182 |
| ion transporter activity | 0 | 15869 | 330974 | 778901 | 957776 | 1167142 | 180847 |
| channel or pore class transporter acti | 0 | 813 | 24053 | 500237 | 1376542 | 2203510 | 393771 |
| antioxidant activity | 0 | 0 | 0 | 6788 | 21683 | 96815 | 13285 |
| oxidoreductase activity | 0 | 2913 | 14793 | 324305 | 1419636 | 2695287 | 9099659 |
| transferase activity | 0 | 672 | 10776 | 149433 | 951290 | 22450688 | 979300 |
| hydrolase activity | 0 | 12419 | 98644 | 359396 | 1276409 | 2848843 | 1203669 |
| lyase activity | 77 | 10885 | 17390 | 51148 | 568656 | 1351083 | 379692 |
| isomerase activity | 0 | 0 | 193 | 15063 | 234557 | 843863 | 219701 |
| ligase activity | 0 | 0 | 6 | 19484 | 315544 | 1100592 | 330559 |
| enzyme regulator activity | 0 | 1114 | 25007 | 55681 | 262072 | 576435 | 116670 |
| transcription regulator activity | 0 | 3822 | 36823 | 92885 | 248734 | 857861 | 159525 |
| translation regulator activity | 0 | 0 | 19 | 29088 | 44889 | 65483 | 13544 |

FIG. 12

Library example: Bioactivity annotation of PubChem compounds G.O. Process

| | score 27 | score 26 | score 25 | score 24 | score 23 | score 22 | score 21 |
|---|---|---|---|---|---|---|---|
| biological_process unknown | 0 | 15996 | 40887 | 15286 | 16059 | 59686 | 6338 |
| development | 0 | 28342 | 253537 | 716385 | 1308320 | 1943767 | 364059 |
| physiological process | 0 | 1403 | 195556 | 916314 | 1875148 | 2873385 | 569565 |
| behavior | 198 | 34605 | 355924 | 723085 | 639465 | 741478 | 103319 |
| metabolism | 0 | 540 | 2211 | 214126 | 1235709 | 2301389 | 655608 |
| catabolism | 0 | 2180 | 10054 | 11156 | 105197 | 316669 | 68674 |
| biosynthesis | 0 | 0 | 49 | 15710 | 315536 | 1014521 | 300801 |
| pathogenesis | 0 | 2180 | 11384 | 67318 | 170416 | 588308 | 132143 |
| cellular process | 198 | 97030 | 741665 | 1731806 | 2718587 | 3446377 | 1077203 |
| cell differentiation | 0 | 12 | 1595 | 122701 | 788274 | 1410128 | 215008 |
| macromolecule metabolism | 0 | 78 | 4444 | 66108 | 372248 | 1116652 | 439101 |
| secretion | 0 | 1 | 11480 | 70182 | 56843 | 35007 | 4822 |
| regulation of biological process | 0 | 11402 | 189000 | 711117 | 1315999 | 1676585 | 267610 |
| cellular physiological process | 77 | 61946 | 775127 | 1953107 | 3400815 | 3959376 | 2351247 |
| response to stimulus | 0 | 2311 | 211647 | 986589 | 2113675 | 2966214 | 903314 |

ESTIMATION OF PROTEIN-COMPOUND INTERACTION AND RATIONAL DESIGN OF COMPOUND LIBRARY BASED ON CHEMICAL GENOMIC INFORMATION

The present application is a Continuation-In-Part application of PCT/JP2007/060736, filed May 25, 2007 claiming the benefit of Japanese Patent Application No. 2006-147433, filed May 26, 2006, the contents of each being hereby incorporated herein by reference.

TECHNICAL FIELD

The present invention relates to a data processing method for efficiently screening using two types of chemical substance databases and for rational design. In detail, the present invention relates to a data processing method for an estimation of compound-protein interaction using both chemical substance information, such as a chemical property of the compound, and biological information, such as sequence information of genes.

BACKGROUND TECHNOLOGY

At present when the human genome is disclosed, a pharmaceutical application utilizing the human genome attracts attention. For drug development based upon the genomic information, it is essential to ascertain an interaction between protein (gene) and a compound; however, massive labor is required to experimentally ascertain these interactions. As a prior art for estimating the interaction between protein and a compound, in general, an estimation system using a conformational model is known (Non-patent Literatures 1 to 4). This system is a method to estimate a stable complex structure with ligand and its strength of binding, and it is referred to as a docking study.

In Published Japanese translation of PCT International Publication for Patent Application 2002-530727 (Patent Literature 1), it is described to specify a high activity region in chemical space and to structure a library. However, this method is merely a definition of the chemical space using only chemical information (such as structure activity correlation information or pharmacophore information).

Further, with a conventional method (Non-Patent Literature 5) by the inventor himself, after a compound group and a protein group are statistically processed separately, such as cluster analysis, compound processed data and protein processed data are integrated and they are displayed on a two-dimensional map, and an interaction pair of protein and the compound is presumed.

NIH of the US has started a chemical genomic project as a national project in 2004. Since then, the application of the genomic information to a chemical field has been focused upon over the world but mainly in the US and Europe. Therefore, at least in the developed countries, such as the US, an efficient estimation method is in demand.

[Patent Literature 1] Published Japanese translation of PCT International Publication for Patent Application 2002-530727

[Non-patent Literature 1] Yoshifumi Fukunishi, Yoshiaki Mikami, and Haruki Nakamura. "The filling potential method: A method for estimating the free energy surface for protein-ligand docking" J. Phys. Chem. B. (2003) 107, 13201-13210.

[Non-patent Literature 2] Shoichet B K, D L Bodian, and I D Kuntz. "Molecular docking using shape descriptors." J. Comp. Chem., 1992. 13(3), 380-397.

[Non-patent Literature 3] Jones G, Willett P, Glen R C, Leach A R, and Taylor R. "Development and validation of a genetic algorithm for flexible docking." J. Mol. Biol. 1997. 267(3):727-748.

[Non-patent Literature 4] Rarey M, Kramer B, and Lengauer T. "Time-efficient docking of flexible ligands into active sites of proteins." Proc. Int. Conf. Intell Syst. Mol. Biol. 1995; 3:300-308.

[Non-patent Literature 5] Okuno Y, Yang J, Taneishi K, Yabuuchi H, and Tsujimoto G. "GLIDA:GPCR-Ligand database for Chemical Genomic Drug Discovery" Nucleic Acids Research, 34, D673-677, 2006.

SUMMARY OF THE INVENTION

The estimation method using a conformational model of protein has problems where it is impossible to cyclopaedically calculate combinations of compound groups having infinity variations and protein groups because an estimation having scientific grounds unless a reliable conformational structure is obtained using the X-ray crystallographic analysis; and in addition, the calculation using the conformational structure has a high load and a calculation time is enormous.

Further, in the technique based upon only the chemical substance information of compounds, the estimation performance is low and greater efficiency is required. The objective of the present invention is to rationally and efficiently screen compounds.

The data processing method of the present invention is a data processing method, wherein a first chemical substance is a compound;

a second chemical substance is nucleic acid, protein or a complex thereof;

a first characteristic amount is expressed as a vector comprised of one or more one type of chemical substance information of the first chemical substance;

a second characteristic amount is expressed as a vector comprised of one or more type of biological information of the second chemical substance; and the first characteristic amount and the second characteristic amount are map-transformed using a multivariate analysis technique or a mechanical leaning method so as to increase a correlation between first space expressing the first characteristic amount and second space expressing the second characteristic amount.

Further, another data processing method of the present invention is a data processing method for determining whether or not the first chemical substance interacts with the second chemical substance, and comprises the following processes (A)-(C):

(A) a process of map-transforming, regarding the first chemical substance and the second chemical substance, which have been known as interacting with each other, the first characteristic amount of the first chemical substance and the second characteristic amount of the second chemical substance, so as to increase a correlation between the first space representing the first characteristic amount and the second space representing the second characteristic amount using a multivariable analysis technique or a machine learning method;

(B) a process of mapping the first chemical substance into the first space representing the first characteristic amount after the map transformation (A) by map-transforming the first characteristic amount of the first chemical substance to be estimated for interaction; and of mapping the second chemical substance into the second space representing the second characteristic amount after the map transformation (A) by map-transforming the second characteristic amount of the second chemical substance to be estimated for interaction; and (C) a process of determining whether or not the first chemical substance interacts with the second chemical substance according to a coordinate position of the first characteristic amount after the map transformation (B) of the first chemical substance to be estimated for interaction and a coordinate position of the second characteristic amount after the map transformation (B) of the second chemical substance to be estimated for interaction.

Further, another data processing method of the present invention is for selecting a chemical substance, which is estimated as interacting with a chemical substance to be estimated at the query side, and comprises the following processes (A), (B), (C1), (D1) and (E1) or (A), (B), (C2), (D2) and (E2): (A) a process of map-transforming, regarding the first chemical substance and the second chemical substance, which have been known as interacting with each other, the first characteristic amount of the first chemical substance and the second characteristic amount of the second chemical substance, so as to increase the correlation between the first space representing the first characteristic amount and the second space representing the second characteristic amount, using a multivariable analysis technique and a machine learning method; (B) a process of mapping a process of mapping the first chemical substance into the first space representing the first characteristic amount after the map transformation (A) by map-transforming the first characteristic amount of the first chemical substance to be estimated for interaction; and of mapping the second chemical substance into the second space representing the second characteristic amount after the map transformation (A) by map-transforming the second characteristic amount of the second chemical substance to be estimated for interaction; (C1) a process of calculating, in the case that the first chemical substance is at a query side out of the subjects to be estimated for interaction, a region where the first characteristic amount of the first chemical substance to be estimated for interaction occupies as a focused region in the first space; (D1) a process of calculating a target region corresponding to the focused region of the first space, in the second space; (E1) a process of selecting the second chemical substance existing within the target region out of the second chemical substance mapped to the second space; or (C2) a process of calculating, in the case that the second chemical substance is at a query side out of subjects to be estimated for interaction, a region where the second characteristic amount of the second chemical substance to be estimated for interaction occupies as a target region in the second space; (D2) a process of calculating a goal region in the first space corresponding to the target region in the second space; and (E2) a process of selecting the first chemical substance existing within the focused region out of the first chemical substance mapped to the first space.

Further, the data processing method of the present invention is a data processing method, wherein a first chemical substance is a compound; a second chemical substance is nucleic acid, protein or a complex thereof; a first characteristic amount is expressed as a vector comprised of one or more type of chemical substance information of the first chemical substance; a second characteristic amount is expressed as a vector comprised of one or more type of biological information of the second chemical substance; and a feature space is constructed by map-transforming the first characteristic amount and the second characteristic amount using a multivariate analysis technique or a mechanical leaning method.

The characteristic amount to be map-transformed may be a characteristic amount where the first characteristic amount and the second characteristic amount are linked.

Another data processing of the present invention is a data processing method, wherein using the feature space constructed using the data processing method, the first characteristic amount of the first chemical substance to be estimated for interaction and the second characteristic amount of the second chemical substance to be estimated for interaction are mapped to the feature space by map transformation using a multivariable analysis technique or a machine learning method; and whether or not the first chemical substance to be estimated for interaction interacts with the second chemical substance to be estimated for interaction is determined according to the position of the first characteristic amount within the feature space and the position of the second characteristic amount within the feature space. Further, the characteristic amount to be mapped to the feature space may be a characteristic amount which is the first characteristic amount of the first chemical substance to be estimated for interaction and the second chemical substance to be estimated for interaction are linked.

Further, the library of the present invention is designed from an obtained determination result or a selected chemical substance by the data processing method. Further, the data processing program of the present invention is a program for causing a computing machine to execute the data processing method. Further, the production method for chemical substances of the present invention is to synthesize a calculation subject of chemical substance estimated as interacting with the query side of chemical substance for estimation of interaction using the data processing method. In addition, the compound of the present invention is a compound produced by using the data processing method.

Efficacy of the Invention

According to the present invention, a calculation technique for estimating the interaction between a compound and protein using both chemical substance information, such as chemical characteristics of compounds, and biological information, such as genomic information, was able to be developed. In this technique, unlike the conventional type estimation using only chemical characteristic information of compounds, the accuracy of the estimation was successfully improved by adding sequence information of genes.

Therefore, this calculation technique is applicable to the following two:

1) A rational design based upon bioactivity of compound library can be realized; and
2) A search for lead compound with better performance than the conventional method can be provided.

Hereafter, preferred embodiments of the present invention are described, and it should be recognized that a person with ordinary skills in the art pertaining to the present invention can appropriately implement the embodiments from the description of the present invention and publicly-known conventional technology in the technical field, and can easily understand the operation and effect of the present invention. Therefore, it is understood that advantages of the present invention are evident to a person with ordinary skills in the art pertaining to the present invention by reading and understanding the detailed description mentioned below with reference to attached documents as occasion demands.

BRIEF DESCRIPTION OF DRAWINGS

FIG. 11 shows results of the bioactivity estimation of PubChem compound.

FIG. 12 shows results of the bioactivity estimation of PubChem compound using a different standard for function categorization of target protein.

BEST MODE FOR CARRYING OUT THE INVENTION

Figure 1:
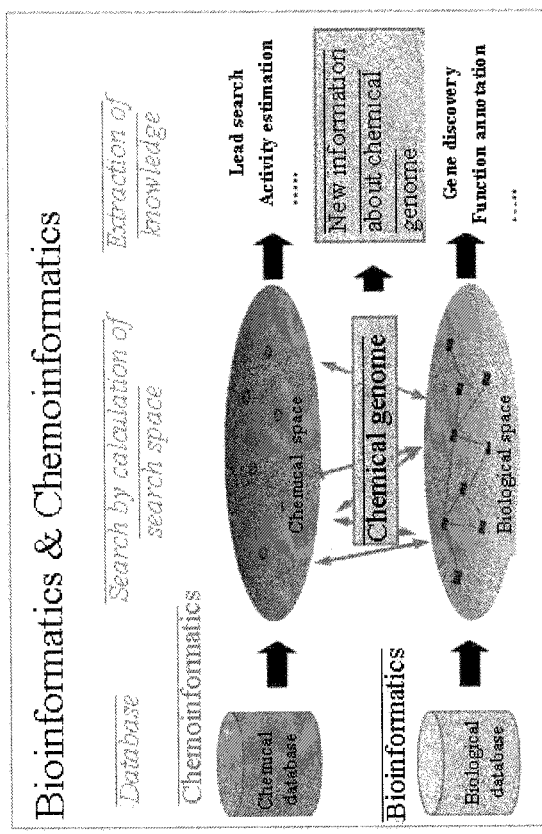
FIG. 1 is a conceptual diagram of the present invention.

Hereafter, the present invention will be described. It should be understood throughout the entire specification that the expression as a singular form also includes a concept of its plural form as long as not particularly mentioned. Therefore, articles or adjectives of a singular form (for example, in the case of English, "a", "an" and "the") should be understood as including the concept of its plural form as long as particularly mentioned. Further, terminology used in the specification should be understood as used with a meaning normally used in the technical field as long as particularly mentioned. Therefore, as long as defined in other field, all technical terms and engineering and scientific terms used in the present specification have the same meanings as generally understood by a person with ordinary skills in the art pertaining to the present invention. If the meaning is inconsistent, the one in the present specification (including definition) has priority.

"Chemical substance" in the present specification is a term in the case of handling a substance especially from an chemical standpoint among general terms of substances, and is referred to as a substance having any certain molecular structure.

"Space coordinates" in the specification are an index for specifying a position of a target within space, "space" is alias of an assembly, and it assumes a type of phase or geometric framework. The space is defined, for example, from chemical substance information or biological information.

As the space, chemical space defined from chemical substance information, such as a compound descriptor or chemical characteristics, expression information, pathway information, functional information and biological space (Current Opinion in Chemical Biology 2005, 9: 296-303) defined from biological information, such as bioactivity can be exemplified.

"Characteristic" in the specification means a special feature of a chemical substance. The characteristic, for example, can include physical properties, such as a melting point, a boiling point or specific gravity; chemical properties, such as reactivity, acidity or alkalinity; and biological properties, such as a protein conformation, enzyme activity, binding capacity with a receptor, cytokine capacity, or interaction force between cells, can be exemplified; however, the characteristics are not limited to these.

In the specification, "simple relevancy cannot be confirmed" between the first characteristic and the second characteristic means that no intuitive correlation is confirmed between both. When a vector indicating the first characteristic is regarded as a, b and a vector indicating the second characteristic is x, y, it is assumed that the pairs of a and x, a and y, b and x and b and y have no intuitive correlation. However, there is a case that correlation is confirmed between linear combination vectors m*a+n*b and M*x+N*y (m, n, M and N are coefficients other than 0). In other words, even if a simple relevancy is not confirmed between the first characteristic and the second characteristic, there is a case that a correlation is confirmed between F (a, b, . . . ) and F' (x, y, . . . ) where an appropriate conversion is added.

"Compound" in the specification means a pure substance that can be broken down into single bodies of two types or more of elements due to a chemical change. This may also be referred to as a pure substance that is generated by a chemical binding with atoms in two types or more of elements. Normally, a relative proportion of each element is uniform in general in accordance with the law of definite composition; however, a compound that creates stable crystal even if the relative proportion is continuously changed within a certain range, like a non-stoichiometric compound, is also included in the category of a compound in the specification.

"Biological material" in the specification means an arbitrary substance relating to organisms. The biological material is also regarded as a type of chemical substance. "Biological object" in the specification means a biological organic body, and it includes animals, plants, fungi and virus; however, it is not limited to these. The biological material includes protein, polypeptide, oligopeptide, peptide, polynucleotide, oligonucleotide, nucleotide, nucleic acid (for example, including DNA, such as cDNA or genome DNA, and RNA, such as mRNA), polysaccharide, oligosaccharide, lipid, and complex molecule of these (such as glycolipid, glycoprotein or lipoprotein); however, it is not limited to these. Normally, the biological material can be nucleic acid, protein, lipid, sugar, proteolipid, lipoprotein, glycoprotein and proteoglycan.

"Receptor" in the specification is a molecule that exists on a cell or within the nucleus, and that has a binding capacity to a factor from the outside world or a factor within the cell, and where a signal is transmitted due to the binding. The receptor normally has a form of protein. A binding partner of the receptor is normally referred to as ligand.

"Agonist" in the specification is a factor that binds a receptor of one ligand, and expresses an action, which is the same level or similar action of said substance. Further, "antagonist" is a factor that antagonistically functions the binding to a receptor of one ligand, and the antagonist itself does not express a physiological action via the receptor. An antagonist, a blocker and an inhibitor are included in this antagonist.

To "convert coordinates" "so as to maximize the correlation" in the specification means a situation where the relationship between each element in one space and each element in another space is correlated at maximum as a whole. This definition can be accomplished by various calculation techniques.

"Correlation" in the specification generally means a relevancy between/among two or more variates in mathematic statistics and biostatistics, and means a linear covariant relationship between two probability variates. In the numeric taxonomy, this can be expressed with a similar coefficient (degree of similarity) between two operational taxonomic units (OTU) to be a target. Therefore, the correlation analysis is a statistical strategy to verify whether or not there is correlation based upon a pair of data or to estimate the magnitude of correlation.

"Coefficient of correlation" in the specification means an invariant quantity with a linear transformation indicating the correlation between two probability variables X and Y. This is a value where covariance of X and Y is divided by a square root of product of variance of X and Y, respectively. For "correlation function", there are space correlation function and time correlation function. An average value $A(r)A(r')$ of a product of physical quantities $A(r)$ and $A(r')$ at two points is referred to as a space correlation function. When this exponentially varies relative to the distance between the two points, this is expressed as follows:

$$\overline{A(r)A(r')} \propto \exp\left(-\frac{|r-r'|}{\xi}\right)$$

Then, the correlation distance $\xi$ is defined. For the time correlation function, the correlation time $\tau$ is similarly defined. The correction distance $\xi$ and the correction time $\tau$ diverge at a critical point.

"Correlation distance" in the specification means distance to be a rough indication of attenuation when the correlation function $<A(r)A(r')>$ of the probability variance $A(r)$ existing at each point of the space decreases as an absolute value along with the increase of the distance between two points $r=|r-r'|$. When the correlation function is a form of $\exp(-r/\xi)$, $\xi$ represents the correlation distance. When the attenuation is not exponential, it cannot be unambiguously defined; however, in many cases, this will be defined as a scale of appropriate length.

As a method to maximize the correlation in the specification, a multivariate analysis technique and a mechanical learning method, such as canonical correlation analysis (CCA), kernel canonical correlation analysis (kernel CCA) or support vector machine (SVM), are available.

"Chemical substance information" in the specification means information as a compound of chemical substance. To be defined in more detail, it includes chemical structure itself and various descriptors calculated by calculation processing from a chemical structure (literature: Handbook of Chemoinformatics: From Data to Knowledge Gasteiger, Johann (EDT)/Publisher: John Wiley Published 2003/10). Normally, information is expressed as a numerical value or a numerical value sequence (vector), respectively. Each compound is expressed as a numerical value sequence (vector) where numerical value sequences of various pieces of appropriately-selected chemical substance information are linked.

Normally, the chemical substance information is defined by a compound descriptor. As the descriptor, for example, one selected from a group comprising a one-dimensional descriptor, a two-dimensional descriptor and a three-dimensional descriptor can be exemplified. "Descriptor" includes a method to describe certain information and the expressed matter. The descriptor can be expressed by radio waves, magnetic waves, sound, lights, colors, images, numerical values, characters or a combination of these. The identification of descriptor group to characterize a molecular structure is an important process in the process to analyze many compounds. Although many descriptors are proposed, these can be classified according to the approach to the molecular structure (see M. Hassan et al., Molecular Diversity, 1996, 2, 64; M. J. McGregor et al., J. Chem. Inf. Comput. Sci., 1999, 39,569; R. D. Brown, Perspectives in Drug Discovery and Design, 1997, 7/8, 31. They are incorporated in the specification as a reference at first. See R. D. Brown et al., J. Chem. Inf. Comput. Sci. 1996, 36, 572; R. D. Brown et al. J. Chem. Inf. Comput. Sci. 1996, 37, 1; D. E. Patterson et al., J. Med. Chem. 1996, 39, 3049; S. K. Kearsley et al., J. Chem. Inf. Comput. Sci. 1996, 36, 118. They are incorporated in the specification as a reference). The one-dimensional (1D) characteristic indicates overall molecular characteristic, such as molecular weight or clogP. The two-dimensional (2D) characteristic includes functionality and connectivity of molecules. As an example of the 2D descriptor, MDL substructure key (see MDL Information System Inc., 14600 Catalina St., San Leandro, Calif. 94577; M. J. McGregor et al., J. Chem. Inf. Comput. Sci., 1997, 37, 443. They are incorporated in the specification as a reference) and MSI50 descriptor (Molecular Simulations Inc., 9685 Scranton Road, San Diego, Calif. 92121-3752) are exemplified. For example, useful and publicly-known five rules (rule of five) on the occasion of identifying elements to a drug compound are derived from the one-dimensional descriptor and the two-dimensional descriptor (see C. A. Lipinski et al., Advanced Drug Delivery Reviews, 1997, 23, 3. This is incorporated in the specification as a reference).

For the calculation of three-dimensional (3D) descriptor, at least one three-dimensional structure having appropriate energy is required. In addition, the three-dimensional descriptor may be calculated by taking contribution from a plurality of conformations into consideration. Further, a descriptor may be selected based upon an important characteristic in the ligand binding or according to other important desired characteristic. Alternatively, in the case of using many descriptors for the analysis of many compound groups, the minimum number of important descriptors should be obtained by a statistical tool, such as principal component analysis (PCA) or partial least squares (PLS).

"Biological information" in the specification means information relating to a biological characteristic, which is a biological material, such as gene or protein, in a chemical compound. The biological information includes, for example, base sequence information of gene, primary structural information, secondary structural information, tertiary structural information, quaternary structure information, conformational information, manifestation information, pathway information, function information and bioactivity information. In the present invention, this biological information is expressed as a numerical value sequence (vector) having numerical values digitalized by calculation processing or measurement as each element.

The characteristic of the biological substance can be expressed by a unique descriptor using the biological characteristic as an index. Therefore, in the specification, "index" regarding one state is a function to be a mark for expressing said state. In the specification, for example, in the case of organism or cell, various physical indexes of the organisms or inside the cell (potential, in vivo temperature, traveling speed/distance, localization rate, ellipticity, elongation rate and revolution speed); chemical index (genome dosage, quantity of transcript of specific gene (for example, mRNA, translated protein, modified protein after translation, ion concentration and pH), quantity of metabolic product and ion content); and biological index (such as individual difference, evolutionary rate or drug response); or reactivity or resistance properties, such as environment of the organism or cell, for example, temperature, humidity (for example, absolute humidity or relative humidity), pH, salt concentration (for example, concentration of entire salt or concentration of specific salt), nutrition (for example, quantity of vitamin, quantity of lipid, quantity of protein, quantity of carbohydrate and metallic ion concentration), metal (for example, quantity of entire metal or concentration of specific metal (for example, heavy metal or light metal)), gas (for example, quantity of entire gas or quantity of specific gas (for example, oxygen, carbon dioxide or hydrogen)), organic solvent (for example, quantity of entire organic solvent or concentration of specific organic solvent (for example, ethanol, DMSO or methanol)), pressure (for example, local pressure or overall pressure (atmospheric pressure or water pressure)), viscosity, flow rate (for example, flow rate of a culture medium in the case that the organism exist in the culture medium, membrane flow), luminosity (a quantity of one specific wavelength), light wavelength (for example, other than a visible light, ultraviolet rays and infrared rays can be included), electromagnetic wave, radiation, gravity, tension, sound waves, organisms other than the target organism (for example, parasite, disease-causing bacterium, bacteria, virus), chemical drugs, (for example, drugs, food additives, agricultural chemical, fertilizer, environmental endocrine disrupter, antibiotics, natural products, psychological stress and physical stress can be used as "index" regarding the state.

"Gene" in the specification means a factor to specify a genetic character. Genes are arranged on a chromosome in certain order. The gene for specifying a primary structure of protein is referred to as structural gene, and the gene affecting the manifestation is referred to as a regulatory gene. In the specification, under a specific situation, "gene" may indicate "polynucleotide", "oligonucleotide" and "nucleic acid" and/or "protein", "polypeptide", "oligopeptide" and "peptide".

"Primary structure" in the specification means an amino-acid sequence of specific peptide. "Secondary structure" means a three-dimensional structure locally arranged within polypeptide. These structures are generally publicly-known as domains. The domain forms a dense unit of polypeptide, and is mainly a portion of polypeptide with 50 to 350 amino acid length. The typical domain is β-sheet and α-helix. "Tertiary structure" means a complete three-dimensional structure of polypeptide monomer. "Quaternary structure" means a three-dimensional structure formed by noncovalently-assembly of independent tertiary unit.

For a mathematical treatment used in the specification, for example, the publicly-known technology described in Mathematics for Life System Analysis, Corona Publishing Co., Ltd., Kazuyuki Shimizu (1999) is applicable.

"Library" in the specification is a certain assembly of chemical substances, such as compounds or organisms, for screening. The library may be an assembly of compounds having a similar nature or an assembly of random compounds. Preferably, an assembly of compounds, which expectedly have a similar nature, is used; however, the assembly is not limited to this.

"Interaction" in the specification means an action between one molecule and another molecule in the case that two or more molecules exist. As such interaction, hydrogen bond, Van der Waal's forces, ionic interaction, nonionic interaction, receptor ligand interaction, electrostatic interaction and host-guest interaction can be exemplified; however, the interaction is not limited to them. As one of techniques for quantifying the intermolecular interaction, thermodynamic or kinetic quantification evaluation method for intermolecular interaction can be exemplified; however, the technique is not limited to this. As the thermodynamic or kinetic quantification evaluation method for intermolecular interaction, for example, calorimetry, surface plasmon resonance method and ultracentrifugal analysis method can be exemplified; however, the method is not limited to these. The intermolecular interaction is expressible with an index indicating a change in thermodynamic quantity between a state where a complex is formed and another state where the complex is dissociated, and for example, it is expressible with a binding constant, a dissociation constant, a change in standard chemical potential associated with binding/dissociation, a change in enthalpy and a change in the number of ion bindings.

"Interaction information" in the specification is, for example, expressed with a presence of intermolecular binding, binding activity and pharmacological activity; however, this information is not limited to them. "Pharmacological activity" is an index indicating potency of drug in general. For example, it is provided as 1050, which is concentration indicating 50% of inhibitory effect on physiological activity, or EC50, which is concentration showing 50% of increase effect on physiological activity, and for "presence of binding" and "binding activity", for example, it is provided as a dissociation constant Kd.

"Information processing" or "processing" in the specification means to convert or integrate from one form to another form for the purpose of easily handing information. Further, "data processing" means a process to convert or integrate data from one form to another form.

"Pattern recognition" in the specification is one of natural information processing. For example, this is to identify and recognize information, which will not be provided as a simple quantity, such as mode, figure, object, image, sound or physiological phenomenon. Such information is referred to as "pattern information" or simply "pattern". As a classifier for conducting the pattern recognition, for example, it is possible to use a technique for comprising a classification parameter from a large quantity of data according to machine learning, such as a support vector machine (SVM), Bayesian classifier. "Interaction pattern" in the specification means information to be defined as a statistic model according to the classifier in the specification.

"Model" in the specification means a mathematical or physical system in accordance with a specific condition, and the model is used for understanding the system in the natural science, such as physics or biology. In particular, in the case of becoming a target for statistic analysis, the model is referred to as "statistic model". In the case that this is used in the specification, "modeling" of a phenomenon is to introduce "model" for elucidation, estimation and control of the phenomenon behind the data and discovery of new knowledge.

In the specification, when an element in an assembly X is provided, the association with one element in an assembly Y by the function $f$ is expressed as "mapping from the assembly X to the assembly Y". Further, the transition from the assembly X to the assembly Y by the function $f$ is referred to as "map transformation". In the present invention, an assembly means an assembly of chemical substances.

Further, "mapping" in the specification is to multiply test data by a calculated weighting factor matrix or a kernel function, by map transformation of training data with a calculation, such as CCA, PCA or becoming kernel.

The library in the specification can be produced or acquired by a technique, for example, a combinatorial chemistry technology, a fermentation procedure or plant and cell extraction procedure. A method to create the combinatorial library is publicly known in the technical field. For example, see E. R. Felder, Chimia, 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37, 177-198; and references cited in these. The entire references are incorporated in the specification as reference.

Associated with the recent development of the combinatorial chemistry and the high throughput screening, it has become possible to experimentally approach many compounds. For example, sec D. K. Agrafiotis et al., Molecular Divesity, 1999, 4, 1; U. Eichler et al., Drugs of the Future, 1999, 24, 177; A. K. Ghose et al., J. Comb. Chem., 1, 1999, 55; E. J. Martin et al., J. Comb. Chem., 1999, 1, 32; P. R. Menard et al., J. Chem. Inf. Comput. Sci., 1998, 38, 1204; R. A. Lewis et al., J. Chem. Inf. Comput. Sci., 1997, 37, 599; M. Hassan et al., Molecular Divesity, 1996, 2, 64; M. J. McGregor et al., J. Chem. Inf. Comput. Sci., 1999, 39, 569; R. D. Brown, Perspectives in Drug Discovery and Design, 1997, 7/8, 31. They are incorporated in the specification as references. Consequently, the technology to analyze a calculation characteristic regarding many compounds has become more and more important in the drug development. In two application examples of specific libraries, i.e., a structure of target library and a structure of primary library, information, which is especially important for a drug design, can be provided by the analysis of calculation characteristic regarding many compounds.

Hereafter, explanation of an embodiment for implementing the present invention is described; however, this embodiment is simply an exemption for implementing the present invention, and it should be understood that the scope of the present invention shall not be limited to such preferred embodiment.

First, the embodiment of the present invention will be explained with reference to drawings.

The technique of the inventors of the present application is integration of a conventional technique using only chemical substance information in the upper stage of FIG. 1 into the bioinformatics technology in the lower stage of FIG. 1, and this is a new interaction estimation method by taking biological information typified by genomic information into consideration.

On the occasion of a search for lead compounds or a library design with a calculation, because similarity of individual compound is reflected, coordinate space showing a relative position is required. For example, the circles on the chemical space on the upper stage of FIG. 1 indicate different compounds, respectively, and compounds whose character is similar are arranged so as to have a relatively-close positional relationship. The coordinate space comprising the positions of these compounds is referred to as chemical space.

Similarly, for protein or gene, space where a similarity relationship is expressed as a relative position is biological space shown in the lower stage of FIG. 1. The square marks in the biological space in the lower stage of FIG. 1 indicate protein or gene. In addition, a model where the chemical space and the biological space are integrated can be created by linking the binding of individual compound and protein (FIG. 1, center arrow).

Figure 2:
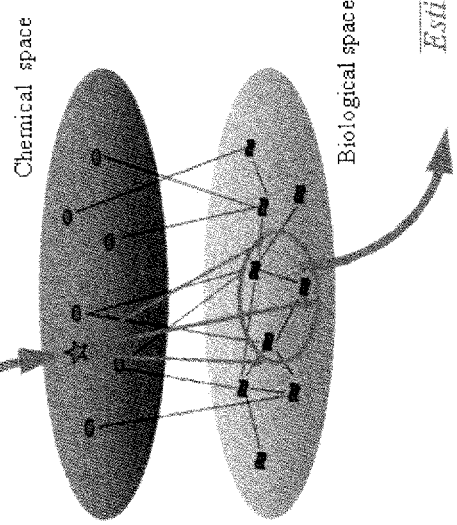
FIG. 2 is another conceptual diagram of the present invention.

FIG. 2 is a conceptual diagram, and shows one example of the embodiment of the present invention. Target protein for a compound to be a query can be estimated from the integrated model of the chemical space and the biological space. First, 1) the compound is mapped to the chemical space coordinate according to the chemical structure of the compound (star mark) of the query (upper stage of FIG. 2). 2) By tracing the link information from the compound adjacent to the compound mapped to the chemical space to the biological space (arrow in the center of FIG. 2), an area (within the circle in lower stage of FIG. 2) within the biological space where the unknown compound is related can be specified. 3) The protein group within this area is assumed as a protein group where this compound with unknown activity is possibly interacted.

Figure 3:
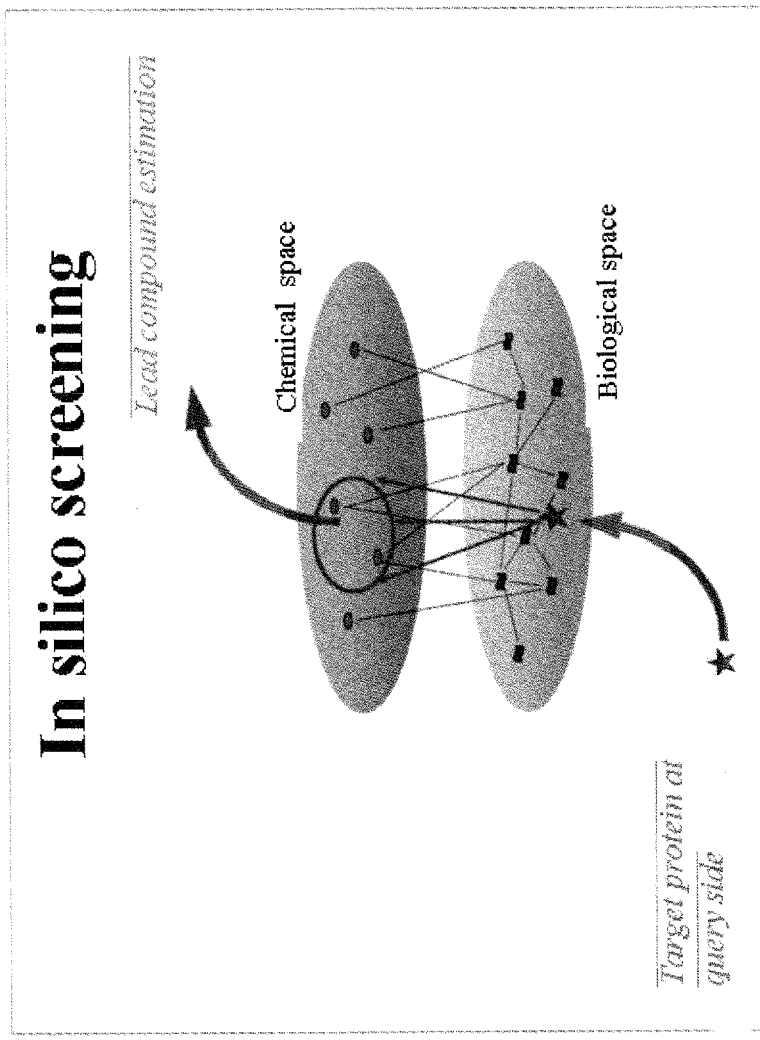
FIG. 3 is another conceptual diagram of the present invention.

FIG. 3 is a conceptual diagram of the present invention showing another embodiment of the present invention. With the integrated model of the chemical space and the biological space, as shown with the arrow in the center of FIG. 3, it becomes possible to predict a lead compound group for interacting with the protein from the query protein.

Figure 4:
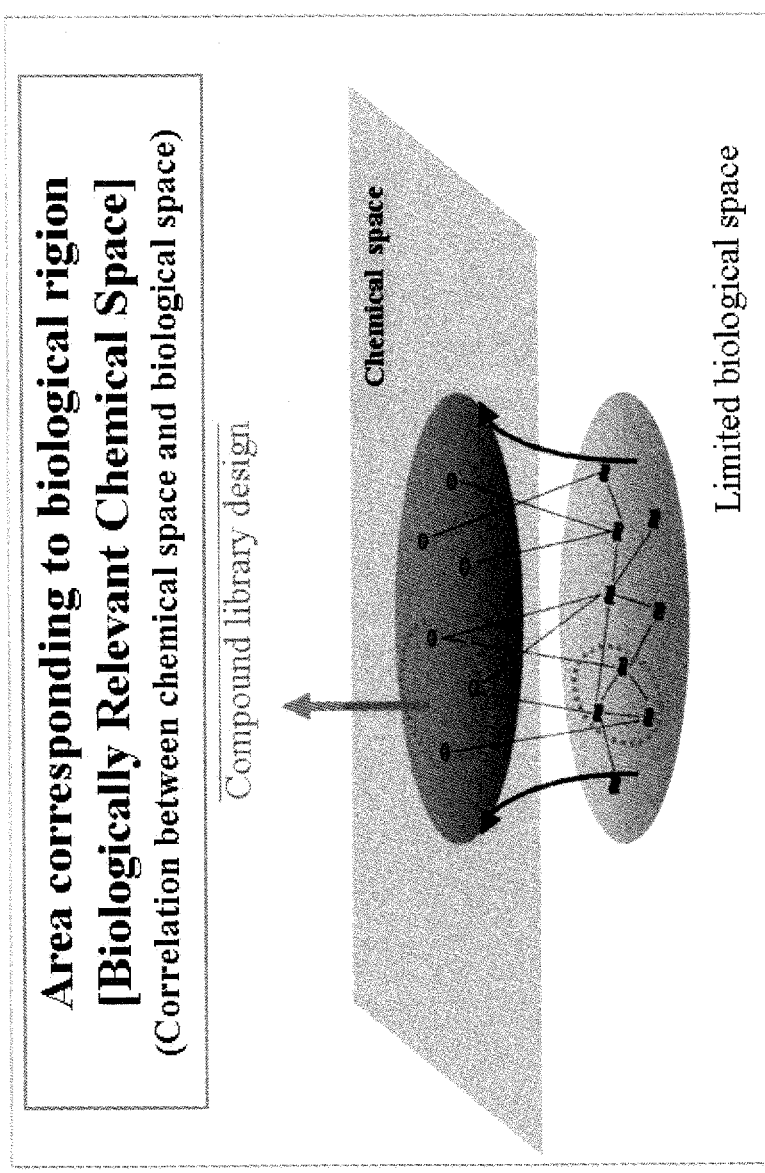
FIG. 4 is another conceptual diagram of the present invention.

In addition, the model where the chemical space and the biological space are integrated is also applicable to a rational design of a compound library. As shown in FIG. 4, it appears that it is highly possible that a compound group within an area (biologically relevant chemical area) corresponding to the limited biological space out of the massive chemical space interacts with the protein group forming the biological space. Consequently, a compound library having bioactivity can be rationally designed. Further, if protein in the biological space is, for example, limited to GPCR family, a focused library can be designed.

Figure 5:
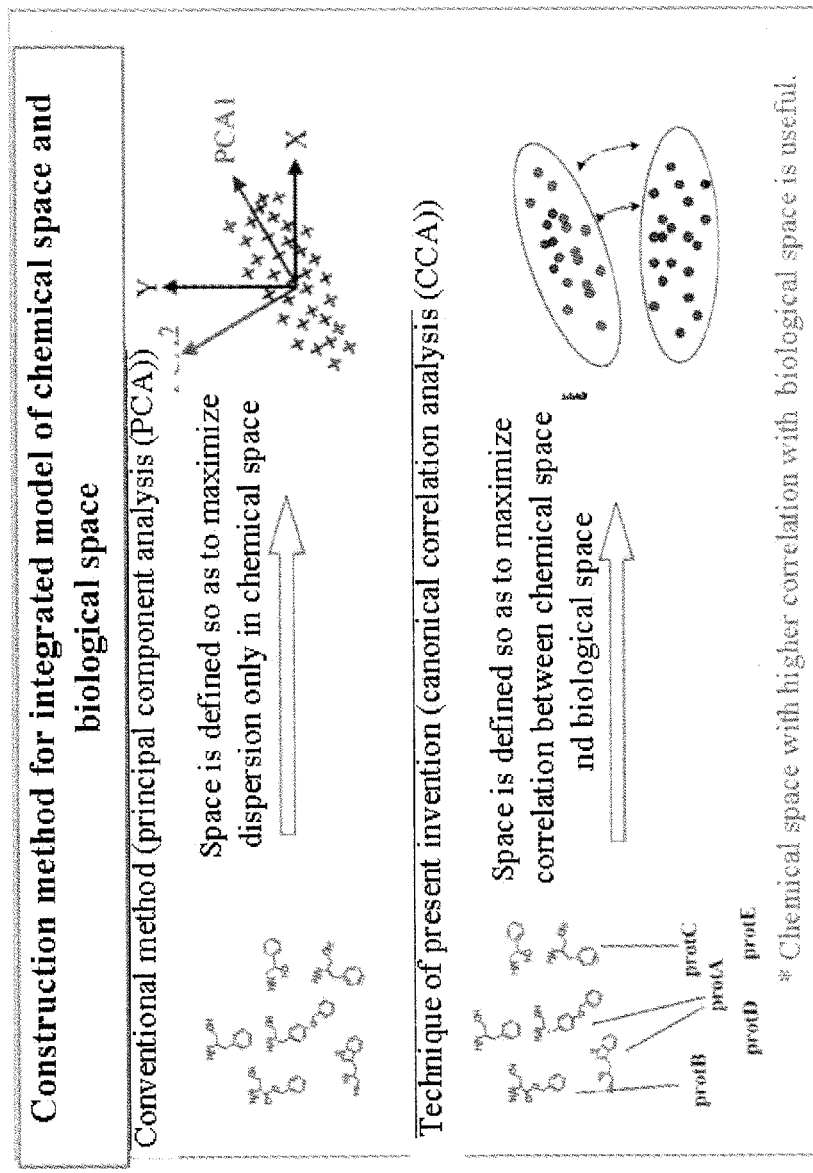
FIG. 5 is a conceptual diagram about a construction method of a model where chemical space and biological space are integrated.

A characteristic of this technique is shown for a construction method for the model where the chemical space and the biological space are integrated. This characteristic will be explained with reference to FIG. 5. The conventional method (upper stage of FIG. 5) defines chemical space coordinates so as to have the chemical characteristic of a compound becoming diversified as much as possible using only the chemical substance information. Howey the point where there is no direct cause-effect relationship between the diversity and the bioactivity of a compound is a problem. Then, this technique is to define both space coordinates so as to increase the correlation between the chemical space and the biological space using both chemical substance information and the biological information. This is because the space coordinates reflecting the bioactivity of the compound can be constructed if the chemical space coordinates are defined by taking the relevancy with the biological space into consideration.

Next, the embodiment of the present invention will be explained in further detail. A first chemical substance is a compound, and a second chemical substance is a biological material, such as nucleic acid, protein or a complex of these. Further, the first space is referred to as chemical space, and the second space is referred to as biological space. As the compound, any compound library can be used. For example, a combinatorial library, any compound library owned by a corporation, database managed by a public agency, compound library database managed by consortium can be exemplified; however, the compounds are not limited to those.

A first characteristic amount is expressed as a vector composed of chemical substance information, and a second characteristic amount is expressed as a vector composed of biological substance information. The first characteristic amount and the second characteristic amount can have no relevancy with each other.

Any information can be used for creation of space coordinates in the present invention. In one embodiment, the space coordinates of a compound in the present invention is defined from chemical substance information. Herein, the chemical substance information is defined with a compound descriptor. The compound descriptor is selected from a group composed of a one-dimensional descriptor, a two-dimensional descriptor and a three-dimensional descriptor. The one-dimensional descriptor is characterized by describing a chemical composition; the two-dimensional descriptor is characterized by describing chemical topology; and the three-dimensional descriptor is characterized by being selected from a group composed of three-dimensional shape and functionality.

Further, the compound descriptor may be pharmacophore. The pharmacophore includes at least three spatially-separated pharmacophore centers. Each pharmacophore center includes (i) a spatial position and (ii) a predetermined pharmacophore type for specifying one chemical characteristic. The pharmacophore type in the basic set includes at least a hydrogen-bond receptor, a hydrogen-bond donor, a negative charge center, a positive charge center, a hydrophobic center, an aromatic center and a default category, which is not included in any other pharmacophore types. Further, the pharmacophore can be described in further detail by providing the spatial position as isolated distance in between the adjacent pharmacophore centers or an isolate distance range.

The chemical substance is expressed as a numerical value sequence (vector) having a compound descriptor, a chemical characteristic to be calculated and pressured from a chemical structure and a descriptor, and numerical values of chemical characteristics obtained by measuring a compound as each element. Therefore, the position of each chemical substance is specified as a vector on the first space coordinates.

The space coordinates of the biological material in the present invention is defined according to biological information. Herein, for the biological information, at least one type of information selected from a group composed of sequence information, a secondary structure, a tertiary structure, a quaternary structure, conformation information, manifestation information, pathway information and functional information can be used. The biological material is expressed as a numerical value sequence (vector) having numerical values digitalized by calculation processing or measurement of the biological information as each element. Therefore, the position of the biological material is specified as a vector on the second space coordinates, respectively.

In a preferred embodiment, the characteristic amount of the first space and the characteristic amount of the second space are map-transformed so as to increase the correlation between the first space and the second space, and more preferably so as to maximize the correlation. Herein, the correlation between the first space and the second space can be increased by a multivariate analysis technique, such as canonical correlation (CCA), kernel canonical correlation (kernel CCA) or a support vector machine (SVM) method, or a machine learning method or an equivalence method thereof.

The canonical correlation analysis (CCA) is a type of the multivariate analysis technique for analyzing the correlation between data sets when two types of foreign data sets, for example, a compound and protein, are provided. CCA is to conduct the map transformation so as to express the correlation between both data sets the best, and then, this results in the analysis of the correlation between the two data. Specific procedures are shown below.

For the specific procedures of CCA, the following can be exemplified: (T. W. Anderson, An Introduction to Multivariate Statistical Analysis, Wiley & Sons, 1984, H. Hotelling, Relations between two sets of variates, Biometrika, 28: 321-377, 1936).

When two types of foreign data (for example, a compound and protein) where an entry of e chemical substance are aligned in a row and chemical substance information is aligned in a column are expressed as matrixes X and Y (the first space is a matrix X and the second space is a matrix Y), $$X = n \times p \text{ matrix}$$

$$Y = n \times q \text{ matrix}$$

$$n \geq p \geq q \geq 1$$

$$f = Xa$$

$$g = Yb$$

$$\sigma_f^2 = \frac{1}{n-1} f'f$$

$$\sigma_{fg} = \frac{1}{n-1} f'g$$

$$\sigma_g^2 = \frac{1}{n-1} g'g$$

in order to maximize the correlation between the first space and the second space,
a set of coefficient vectors a and b to maximize the correlation is searched, and $$r_{fg} = \frac{\sigma_{fg}}{\sigma_f \sigma_g}$$

herein, $$\sigma_f^2 = \sigma_g^2 = 1$$

with the following conditions:

$$r_{fg} = \sigma_{fg}$$

is maximized, $$r_{fg}$$

is referred to as canonical correlation, and $$f, g$$

To be more specific, in the canonical correlation analysis, a singular value decomposition of X and Y is conducted, $$X = U_X D_X V'_X \quad Y = U_Y D_Y V'_Y$$

$$U'_X U_Y = UDV'$$

U, D and V are calculated, and using U, D and V, the following are acquired:

$$A = \sqrt{n-1} V_X D_X^{-1} U \quad B = \sqrt{n-1} V_Y D_Y^{-1} V$$

$$F = \sqrt{n-1} U_X U \quad G = \sqrt{n-1} U_Y V$$

it is provided that A, B, F and G are as follows:

$$f_i = X a_{i} g_i = Y b_i \; i=1, \ldots, q$$

$$A = [a_1, \ldots, a_q] \; B = [b_1, \ldots, b_q]$$

$$F = [f_1, \ldots, f_q] \; G = [g_1, \ldots, g_q]$$

$$F = XA \; G = YB$$

herein, the higher correlation can be obtained from i=1 in order $$r_{fg}$$

The kernel canonical correlation analysis (kernel CCA) is a technique introducing a kernel method to a normal canonical correlation analysis, and with regard to the canonical correlation analysis based upon a linear model, a correlation analysis based upon a nonlinear model is possible with the kernel canonical correlation analysis. This is a method to conduct the canonical correlation analysis to X' and Y' where X in the first space and Y in the second space, which were targets in the canonical correlation analysis (S. Akaho, A kernel method for canonical correlation analysis, International Meeting of Phychometric Society (IMPS), 2001).

The support vector machine (SVM) method is a machine learning algorithm for solving a supervised identification problem (reference: B. E. Boser, I. M. Guyon, and V. N. Vapnik, A training algorithm for optimal margin classifiers, In D. Haussler, editor, 5th Annual ACM Workshop on COLT, pages 144-152). In SVM, it is characterized such that the way of thinking to maximize a margin for obtaining a separated plane (hyperplane) where the distance from each data point becomes maximized in order to classify data into two types is used. In addition, it is also characterized such that a superior performance even in the non-linear separation problem is confirmed by using a method where a pattern is map-transformed to limited or infinite dimensional feature space using the kernel function. Herein, when a supervised classification problem is applied to a binding estimation of protein and a compound, it results in the creation of a classifier to classify a class representing binding between the protein and the compound and another class representing not binding. In this case, known binding data between protein and a compound, which can be obtained from references or experiments, can be used as supervision data.

The multivariable analysis technique is a generic term of statistic technique to be used for acquiring a mutual relationship between variables by utilizing data (multivariable data) having a plurality of variables (item, attribute and number of dimension). Techniques, such as multiple regression analysis, discrimination analysis, canonical analysis, principal component-factor analysis, cluster analysis, multidimensional scaling, face analysis, quantification analysis, or conjoint analysis, are available.

These are effective to "summarize" tendency and/or characteristic in complicated data, for "discovery of a cause" or "presumption/estimation" by clarifying a correlation that affect results, or modeling of cause-effect relationship. CCA and kernel CCA also correspond to this multivariable analysis.

The machine learning approach is one of research projects in artificial intelligence, and is a technology/technique for realizing a function, which is similar to learning capability naturally performed by a human. A sample data assembly with a certain number of samples as targets is analyzed, and useful regulations, rules, knowledge expression and judgmental standard are extracted from the data.

In one embodiment, the present invention provides a data processing method for selecting a chemical substance, which is estimated to interact with one chemical substance.

"Focused region" used in this method indicates a region calculated within the chemical space. "Target region" indicates a region calculated within the biological space.

In the case that protein is at the query side out of estimation targets of interaction, i.e., the case of estimating a compound acting on target protein, will be explained in detail. First, optional activity about protein is selected. When the characteristic of the target protein is selected, any target region within the corresponding space can be calculated.

When the target protein or a target protein group is provided, a protein group whose sequence and structure are homologous with those of the target protein is selected, and a target region can be calculated as a space region where these occupy. Further, in the case of calculating the target region based upon a function defined in protein (for example, gene ontology), a protein group where the same level of function as the target protein or the target protein group is defined is selected, and the target region can be calculated as a space region where these occupy.

In addition, in the case of calculating a target region based upon a gene manifestation pattern, pathway positional information or bioactivity information (for example, microarray data, reaction pathway or pathological activity), a protein group where the gene manifestation pattern, the pathway positional information and bioactivity information, which are the same level as those in the target protein or the target protein group, are defined is selected, and the target region can be calculated as a space region where these occupy.

A process to calculate a focused region in the chemical space existing at predetermined distance or less from the target region will be described. First, a compound group that can bind with each protein within the target region is specified. For each of the specified compounds, a focused region existing at predetermined distance or less within the chemical space is calculated.

The distance herein includes a distance to satisfy a maxim of distance, such as Euclidean distance or Manhattan distance, and a similarity index, such as coefficient of correlation or kernel, as well.

In the process to select a compound existing in a focused region of the chemical space, a compound corresponding to the calculated focused region is selected. This can also be selected by an automatic calculation if the goal region is calculated.

Further, in another embodiment, if compound is at the query side out of the estimation target of interaction, i.e., a method to predict protein to act on a target compound, is provided.

In one embodiment, the present invention further includes a process for training so as to correlate between the first space and the second space using sample data. "Training" in the specification is a calculator operation required for using a device, and an operation used for performing an activity, such as mounting operation, a console operation, a conversion operation or printing operation, or necessary demonstration.

"Training data" in the specification is practice data to be entered into a computer of a robot at the beginning of operation.

In one embodiment, the training generates an orthogonal matrix $A=C_{xx}^{-1/2}U$ and $B=C_{yy}^{-1/2}V$ (herein, $\det(A)=\det(B)=1$ and as shown in the following mathematical expression):

$$C_{xx}=E\{(X-m_x)(X-m_x)^T\}, C_{yy}=E\{(Y-m_y)(Y-m_y)^T\},$$
$$C_{xy}=E\{(X-m_x)(Y-m_y)^T\}, K=_{xx}-\tfrac{1}{2}\cdot C_{xy}\cdot C_{yy}^{-1/2}=U\cdot S\cdot V^T$$

It can be characterized such that the correlation between AX representing the first space of a first modality and BY representing the second space of a second modality becomes maximized, and due to this, it becomes possible to transfer from the first modality to the second modality.

In another embodiment, a matrix A and a matrix B are created according to the training. The correlation between XA representing the first space of the first modality and YB representing the first space of the second modality becomes maximized, and due to this, it becomes possible to transfer from the first modality to the second modality. For the transfer of characteristic, two types of foreign data (for example, a compound and protein) where entries of chemical substance are aligned in the row and chemical substance information is aligned in the column of the matrixes X and Y are expressed as matrixes X and Y (the first space is a matrix X and the second space is the matrix Y), and the canonical correlation analysis is conducted and the correlation between both spaces can be maximized.

"Modality" in the specification means a characteristic attribute. In one embodiment, if only the result of the query of BY representing the second space, since BY has the maximum correlation with AX, it is possible to specify the query of AX representing the first space.

Further, the present invention provides a data processing method for map transformation of the first characteristic amount of the first chemical substance and the second characteristic amount of the second chemical substance into one feature space by the multivariable analysis technique or the machine learning approach. As the machine learning approach, the SVM method can be used.

Further, in the specific embodiment, in the machine learning procedure, 1) a process of mapping the characteristic amount of the first chemical substance and the characteristic amount of the second chemical substance both to be estimated for interaction into feature space constructed with database of the space coordinates of the first characteristic amount of the first chemical substance and database of the space coordinates of the second characteristic amount of the second chemical substance; and 2) a process of determining that the first chemical substance and the second chemical substance are bound in the case that the inquired pair exists within the space area; and determining that the first chemical substance and the second chemical substance are not bound in the case that the inquired pair does not exist within the space area, are included.

The characteristic amount may be a characteristic amount where the characteristic amount of the first chemical substance and the characteristic amount of the second chemical substance are linked. Further, the characteristic amount of the first chemical substance and the characteristic amount of the second chemical substance are expressed with a vector, respectively; however, the linked characteristic amount includes kernel, which is an inner product of vectors.

In one embodiment, the method of the present invention further includes a process of producing a selected chemical substance in silico. The production method in silico is described in another section of the specification, and a publicly-known technology can be used.

In another embodiment, the method of the present invention further includes a process of producing a selected chemical substance in the wet condition. The production method in the wet condition is described in another section of the specification, and a publicly-known technology can be used. As a typical example of production in the wet condition, combinatorial chemistry may be used. The production in the wet condition may be accomplished by using the genetic modification technology.

In one specific embodiment, the method of the present invention further includes a process of measuring the second characteristic amount of the chemical substance in the first space after selecting the chemical substance in the first space, of selecting a chemical substance having an actual desired activity.

In the present invention, the process of determining whether or not the first chemical substance interacts with the second chemical substance includes a process to calculate the interaction probability. Further, the probability of interaction may be calculated as a score. The score herein indicates bindability (statistic significance of binding estimation) between any chemical substance A within the first space and any chemical substance B within the second space.

For example, the binding score of the chemical substance A and the chemical substance B can be defined as mentioned below. It is assumed that the number of all chemical substances within the second space is N, and the number to be bound with the chemical substance A is L. Herein, considering K pieces of chemical substances adjacent to B within the second space, it is assumed that the number to be bound with the chemical substance A is H. The binding score from the chemical substance A to B on that occasion can be defined as odds score, such as $\log((H/K)/(L/N))$. Further, inversely, it is assumed that the number of all chemical substances within the first space is n, and the number to bind with the chemical substance B among them is 1. Herein, in the case of considering k pieces of chemical substances adjacent to A within the first space, it is assumed that the number to be bound with the chemical substance B among them is h. The binding score from the chemical substance B to A on that occasion can be defined as odds score, such as $\log((h/k)/(l/n))$. Therefore, according to the score from the chemical substance A to B and the score from B to A, the overall score of the chemical substances A and B can be defined as $\log((H/K)/(L/N))+\log((h/k)/(l/n))$. These scores can be calculated from the correlation model of the first space and the second space calculated by CCA or kernel CCA. Further, in the case of using the SVM method, the score can be converted from the equivalence of a distance from a hyperplane for separating a known binding pair and a not-binding pair between the chemical substance group within the first space and the chemical substance group within the second space.

"Interaction information" includes a dissociation constant Kd, concentration in 50% inhibitory effect concentration 1050 and 50% increase effect concentration EC50. In the case of drug development, Kd, IC50 and EC50 as the standard of the presence of binding, binding activity and pharmacological activity are micro mole order or nano mole order. Further, the score of probability for interaction is expressed with a distance from a boundary surface (hyperplane) for class classification (for example, a class of binding pair of compound and protein and a class of not-binding pair of compound and protein) within a feature space to the estimation target. The further the distance from the boundary surface becomes, the higher the probability for interaction becomes.

The present invention provides a library designed from the result obtained by the data processing method of the present invention. Further, the present invention provides a chemical substance produced by using the method of the present invention.

Further, the present invention provides a program causing a computer to execute the data processing method of the present invention. The program of the present invention is stored in a computer-readable recording medium. As a recording medium, as long as a program can be recorded, it appears that any format (for example, any type, such as flexible disc, MO, CD-ROM, CD-R or DVD-ROM) can be used. In addition, a data structure used for the data processing method of the present invention is stored in the recording medium. Specifically, a data structure comprising the first space defined by the database of the space coordinates of the first chemical substance and the second space defined by the database of the space coordinates of the second chemical substance and a data structure comprising feature space constructed by the method of the present invention are included.

The present invention is applicable to the objective to search a compound having an activity to specific target protein, and in addition, leads to the estimation of a plurality of proteins acting on a compound when a specific compound is provided, and provides findings regarding side effects of the drug. Further, it appears that an application for creation of artificial protein (genetically-modified protein), which can act on a specific compound(s), is also possible.

Further, a data processing apparatus for estimating the interaction between the first chemical substance and the second chemical substance using the data processing method of the present invention is provided. Further, in another embodiment, a data processing apparatus for selecting a chemical substance, which is estimated to interact with a specific chemical substance, is provided. In addition, in another embodiment, a data processing apparatus to design a chemical substance library is provided. These processors are implemented by executing the method of the present invention on a calculating device equipped with the processor.

References, including overall scientific references, patents and patent applications, cited in the specification are incorporated in this speciation as references to be the same degree as specially described, respectively.

As described above, the present invention has been explained by showing the preferred embodiments for easy understanding. Hereafter, the present invention will be explained based upon examples; however, the above-mentioned explanation and examples hereafter are provided only for the purpose of exemplification, and they are not provided for the purpose of limiting the present invention. Therefore, the scope of the present invention is not limited to the embodiments, which are specifically described in the specification, and the examples, as well, and they are limited only by the claims.

EXAMPLES

Hereafter, the present invention will be explained with reference to the examples; however, the present invention shall not be limited to the examples mentioned below.

Example 1

Screening in biological space and chemical space using CCA

In order to evaluate the performance of the conventional method (PCA) and the present technique (CCA), in-silico screening was conducted using "integrated model of chemical space and biological space" constructed by both methods, respectively.

Figure 6:
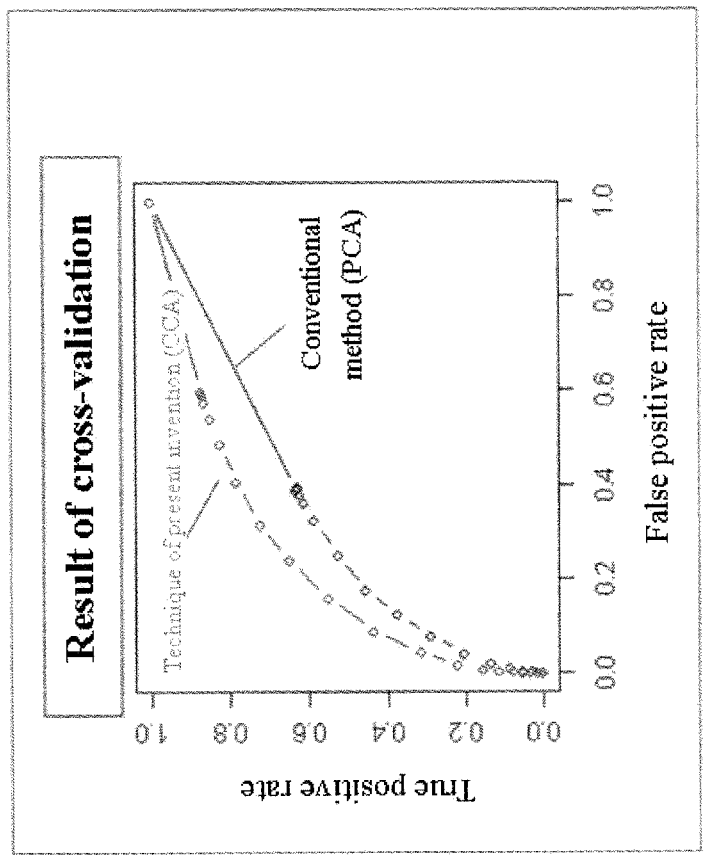
FIG. 6 shows a ROC curve of the result of in silico screening based upon the data acquired from drug bank database for performance evaluation between the conventional method (PCA) and this method.

FIG. 6 shows a ROC curve, which is one of the methods to evaluate the estimation performance. This graph indicates that the more upper the curve is positioned, the better the estimation performance is, and since the curve of the present technique is positioned more upper than that of the conventional method, the estimation performance of the present technique is higher than that of the conventional method. The specific procedures are shown hereafter.

(Protocol)
1. Data of known proteins and compounds to be used for the formulation of integrated model were acquired from Drug Bank Database (http://redpoll.pharmacy.ualberta.ca/drugbank/), version released in August 2005.
2. For a mol file of all compound entries, 936 compound descriptors were calculated using Dragon X software. Herein, the number of calculated compounds is 3,079. In addition, for the purpose of CCA calculation, since the profile of the descriptor to be an attribute has to be independent, the descriptors having correlation with 0.8 or greater of coefficient of correlation were reduced to 300 descriptors with higher information volume.
3. For a fasta file of all protein entries, a 400-dimensional (amino acids: 20 types*20 types) profile composed of relative proportions of two successive amino acids by taking mismatch into consideration was calculated by the technique, which is similar to the technique to generate mismatch string kernel. Herein, the number of profiled proteins is 3,476. Further, the number of binding with the calculated compounds in above-mentioned 2. was 8,006.
4. For the evaluation of estimation performance, a 5-fold cross validation was used. In other words, 8,006 compound-protein binding data prepared in the above-mentioned 2. and 3. were randomly classified into 4:1, and CCA calculation and PCA calculation were conducted using 80% of binding data as training data, and the coordinates of the biological space and the chemical space were formulated. The remaining 20% of binding data was used as test data. Herein, a negative example of test data (not-binding data) generated a combination, which would not be bound with the combinations of compounds and proteins, which form binding data as a positive example, and the same number as the positive examples were randomly selected. The test data prepared as described above was mapped into the biological space and the chemical space formulated by the training data, respectively. For the mapping, a weighting factor matrix (in the case of PCA, principal component score coefficient matrix) is applied to a test data matrix by CCA or PCA calculation of the training data. For the proteins and compounds mapped to the biological space and the chemical space, the score was calculated, respectively.
5. When the test data is estimated as shown in the above-mentioned 4, a proportion for the one, which was able to be estimated to bind the binding data in actuality, is referred to as a true positive rate, and a proportion for the one, which happened to be estimated to bind the not-binding data in actuality, is referred to as a false positive rate. Herein, data having a specific estimation score (threshold) is regarded as positive, and data having a specific estimation score or less is regarded as negative. The threshold of the score was fluctuated based upon the compound-protein binding score estimated in CCA and PCA, and they are plotted as the false positive rate and the true positive rate (x,y) associated with the fluctuation and a ROC curve was created (FIG. 6).

Example 2

Compound-GPCR Interaction Estimation Technique

A compound-GPCR interaction estimation technique was developed with the procedures mentioned below. Furthermore, for references where data sets and analysis methods used in this example are described, reference numbers were marked in the text and a list of references was attached at the end of this example. These references are incorporated in the specification as references.

(#1 Collection of Compound-Protein Interaction Information)

Combinations of interacting compounds-GPCR, 5207 examples (compounds: 866, GPCR: 317) were collected from GLIDA (GPCR-LIgand DAtabase) [1], Drug Bank [2], IUPHAR Reeceptor database [3] and PDSP Ki database [4]. However, herein, human, mouse and rat GPCR were used, and GPCR was defined in accordance with GPCRDB [5]. Further, for the compounds, since structure information was required for the calculation of following descriptor, compounds registered in GLIDA and PubChem Compound [6] providing mol(sdf) format files were used.

(#2 Calculation of Descriptor)

In order to express the compound and protein as a characteristic vector, each descriptor was calculated with the following methods:

Chemical Descriptor

A descriptor regarding the structure and physical property of the compounds were calculated from the structures of collected compounds according to Dragonx ver. 1.2 [7]. In this study, a total of 929 descriptors in categories 1-10 (constitutional descriptors, topological descriptors, walk and path counts, connectivity indices, information indices, 2D autocorrelations, edge adjacency indices, Burden eigenvalue descriptors, topological charge indices and eigenvalue-based indices), categories 17-18 (functional group counts and atom-centered fragments) and category 20 (molecular properties), were calculated. Furthermore, descriptors depending upon the three-dimensional coordinates of molecular (categories 11-14), descriptors counting the number of functional groups and atom types (categories 15 and 16) and an electric charge descriptor (category 19) were not used herein. Subsequently, among these descriptors, ones where all compounds were calculated and outputted as the same value were removed, and 797 types of descriptors remained as a result were used hereafter.

Protein Descriptor

This descriptor was calculated using a spectrum method [8] where mismatch was allowed. In this method, a protein sequence is broken down to an amino acid sequence with fixed length k, and calculation is conducted by counting the frequency of the amino acid sequence pattern with the length k where up to m mismatches are allowed appeared in this sequence. The inventors set (k,m) at (2,1). Therefore, the number of the descriptors to be calculated is 202 types of double amino acids where and amino acid mismatch is allowed.

(#3 Structure of Learning Model by Support Vector Machine (SVM))

SVM is a learning algorithm proposed by Vapnik et al. [9], and it is often used in many fields because of its high generalizing capability. SVM constructs a hyperplane so as to separate characteristic vectors of two different groups by a maximum margin. Herein, the maximum margin indicates the shortest distance from the separated hyperplane to each sample.

The inventors, for obtaining a hyperplane for separating whether or not the compound-protein interaction exists, a characteristic vector was constructed by combining the chemical descriptor and the protein descriptor corresponding to a positive example (interacting pattern) and a negative example (not interacting pattern), respectively, and constructed a learning model using SVM. However, for the negative example, because information of not-interacting pattern was not obtained, two descriptors were combined at random and the negative examples as many as the positive examples were generated. Herein, as the SVM library, codes of libsvm program [12] adopting "Sequential Minimal Optimization" algorithm [10, 11] were used. Once the SVM model is obtained, which class of interaction or no interaction a new vector (a pair of compound and protein) belongs to can be estimated. In addition, not only the determination, a method for sample scoring is also reported [13]. This is based upon a notion where a sample close to a separation plane would have a higher probability to be classified by accident compared to a sample far from the separation plane. The inventors scored and prioritized the possibility using this method in the interaction estimation between compound-protein.

(#4 Ligand Estimation by Compound Structure Similarity)

The inventors used the similarity of the compound calculated from the chemical descriptor as a ligand estimation method to be a model comparison. This similarity is a method for a general compound search, and it is said that this is a help to discover a lead compound [14]. In this study, 797 types of chemical descriptors calculated in #2 were analyzed regarding principal components, and compounds adjacent to the known ligand were sequentially scored on the principal component. The score of a pair of compound A and protein B is expressed with a similarity with the known ligand of the protein B the closest to the compound A. For the principle component, up to components with 80% of accumulated contributing rate (30 principal components) were used. Further, as the similarity scale, a correlation coefficient (Pearson correlation coefficient) was used.

(#5 Evaluation of Model by Cross Validation)

The estimation performance of a learning model was evaluated using n-fold cross-validation. In this validation, at first, all learning data sets are divided into n sub-sets with equal size. Subsequently, each sub-set is estimated using a classifier, which was learned and made with the remaining (n−1) sub-sets. Then, this operation is repeated so as to estimate all sub-sets only once and evaluation is conducted. As the scale of the estimation performance, the accuracy calculated with an expression mentioned below was used. The accuracy is expressed with the following expression.

Accuracy=(TP+TN)/(TP+TN+FP+FN)

Herein, TP, TN, FP and FN represent true positive, true negative, false positive and false negative, respectively.

Taking the score fluctuation by a negative example created with random combination into consideration, ten times of different data sets were created while a negative example was exchanged, and the 5-fold cross-validation was repeated and the model by the inventors was evaluated using a mean value of the accuracy. Subsequently, ROC analysis was conducted from the calculated interaction estimation score. Herein, in each evaluation, the ligand estimation method (#4) based upon the structure similarity of the compound was regarded as a comparison subject.

(#6 Ligand Estimation of Human β2 Adrenaline Receptor (β2AR))

The compound-GPCR interaction information collected by the inventors is only known as "strongly binding" according to the research up to now, and other majority of compound-GPCR interaction is unknown. The question by the inventors is whether or not a compound, which has been estimated as interaction, may not interact in the ligand search. Then, the inventors confirmed the relevancy between the interaction estimation score and the presence of interaction was confirmed according to in vitro binding inhibitory test.

Consequently, human β2AR was regarded as a target protein, and the ligand estimation was conducted using the prepared learning model. This receptor is a physiologically important gene for development of therapeutic drug as a target of asthma therapy. The subject compound for the ligand estimation was the above-mentioned 866 compounds known with the interaction with GPCR (however, a compound where the interaction with human β2AR was learned at the time of model structure was excluded). β2AR protein descriptors were combined with the chemical descriptors of these compounds, and data sets for estimation were obtained. Taking the score fluctuation due to the combination of negative examples into consideration, a trial of the learning and estimation was repeated 30 times while the negative examples were exchanged, and the maximum value of the obtained score was regarded as a final estimation score.

Next, the compounds in the top 50 of interaction estimation scores were further examined and tested. First, whether or not any report regarding the interaction with β2AR was checked according to references and patent search (SciFinder, PubMed).

Subsequently, among the compounds where no interaction information could be confirmed, acquirable compounds were verified using binding inhibitory test in vitro. In this test, a membrane fraction was prepared from the human β2AR forced expression cell strain, and a competitive inhibitory effect on [$^{125}$I]-cyano pindolol, which is radioactive β2AR ligand, was confirmed.

Due to lack of information about no interaction, in the model by the inventors, randomly-generated pair of compound-protein is adopted as a negative example (no interaction) pattern. Consequently, it is necessary to confirm whether or not a compound with a low interaction estimation score does not really interact. Then, the inventors, for the bottom 50 of estimation scores, conducted the reference search and verification test similarly to the top 50 of estimation scores.
(Results)
(Evaluation of New Ligand Estimation Model by Cross Validation)

Figure 7:
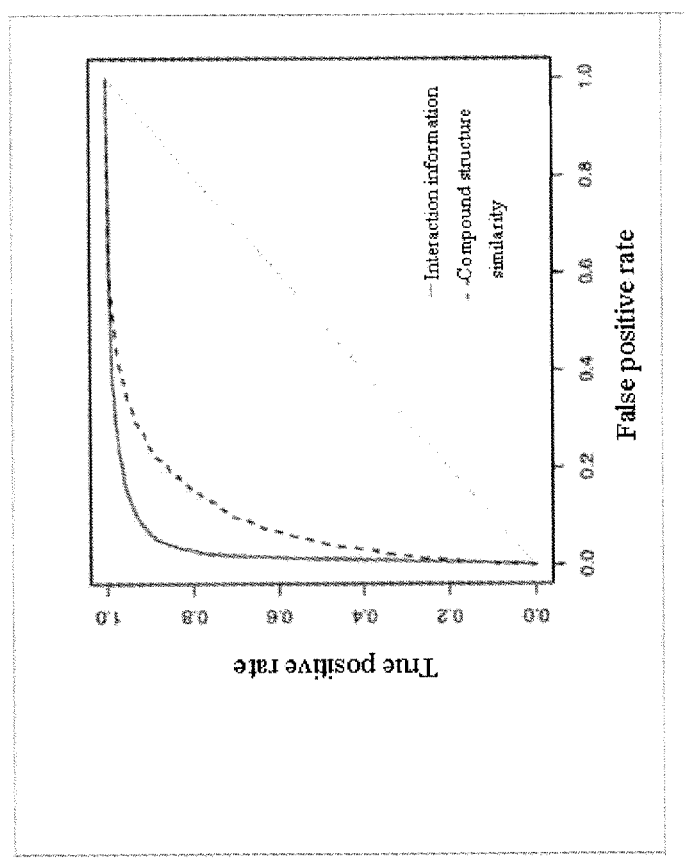
FIG. 7 shows a ROC curve of the result of the interaction estimation based upon the data of collected interacting compound-GPCR for performance evaluation between the conventional method (interaction estimation method by compound structure similarity) and this method.

First, the developed method and the conventional method were compared first. The characteristic vector of the compound-protein interaction pattern was regarded as an input of SVN classifier using the GPCR-ligand interaction information collected from public database, and a learning model was constructed. As a result of trying the 5-fold cross validation while exchanging a negative example 10 times, the estimation performance (accuracy) of the model developed by the inventors was 91.3%+/−0.3%. As a comparison, for the conventional method based upon the compound similarity, the 5-fold cross validation was similarly conducted and the estimation performance 81.9%+/−0.3%. Further, it became ascertained that the estimation performance of the model developed by the inventors is high according to the ROC curve, as well (FIG. 7).
(Human β2AR Ligand Estimation)

Next, the new technique was applied to the new ligand estimation for human β2AR, and the validity was verified from the experiment. Further, whether or not a ligand, which is estimated only by the new technique, includes a compound having a new skeleton, which cannot be detected with the conventional method, was examined. The interaction estimation score with β2AR was calculated using the constructed model, for 866 types of GPCR ligands.

Figure 8:
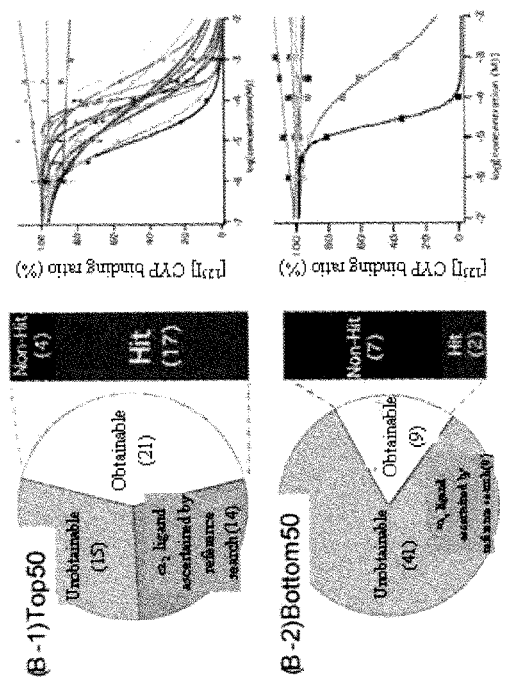
FIG. 8 shows results of verification of β2AR ligand estimation results, and also shows results of examination and experiment to compounds in the top 50 (B-1) and bottom 50 (B-2) of estimation score. The left side shows a breakdown of the compounds ascertained in the literature search and the experimental verification, and the right side indicates a binding inhibition curve to $[^{125}I]$-cyanopindolol, and the vertical axis indicates an inhibition ratio and the horizontal axis indicates a concentration of each compound.

Among the top 50 of β2AR ligand candidates estimated by the new model, reports where 14 types of compounds that interact with β2AR were confirmed according to references and patent search (left (B-1) in FIG. 8). In addition, among the remaining compounds with unknown interaction, the in vitro binding inhibitory test was conducted for 21 acquirable types, and 17 types of compounds showed the interaction ($10^{-5}$ M<$IC_{50}$<$10^{-3}$ M) (right (B-1) in FIG. 8). The rate of hit in the test was up to 81% (17/21), and a high estimation hitting ratio is shown herein.

In the meantime, for the bottom 50 of compounds, compounds reported as β2AR ligand were not confirmed in references and patent search (left (B-2) in FIG. 8). In addition, for 9 acquirable compounds among the remainder compounds, the in vitro binding test was conducted, and two compounds showed the same level of strength; however, the remaining 7 compounds did not show any interaction (right (B-1) in FIG. 8).

Figure 9:
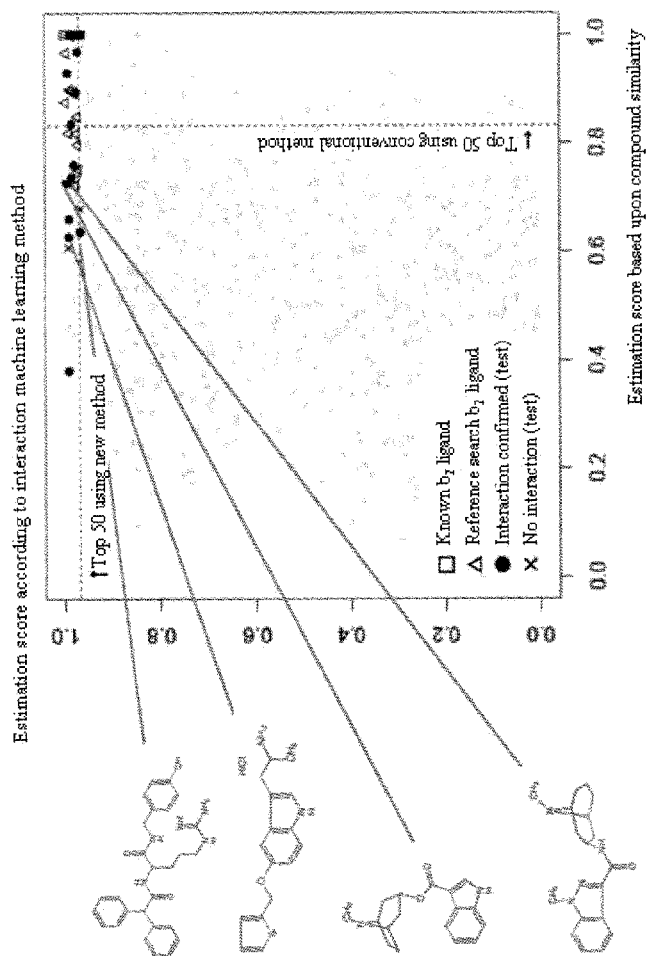
FIG. 9 shows a comparison of the β2AR ligand estimation results between new model and a conventional method. Each point is a compound, and the vertical axis indicates a new model and the horizontal axis shows an interaction estimation score by the conventional method.

FIG. 9 is a graph where these estimation results are compared to that with the conventional method. Nearly one-half of compounds where the interaction was confirmed with the tests shows lower scores with the conventional method based upon the structure similarity of compounds. In actuality, these compounds have various skeletons (left of FIG. 9), which are different from those in the structure of the typical β2AR agonist (catecholamine skeleton, isoprenaline derivative) and the structure of the β2AR antagonist (arylalkyl amine derivative), and this can be considered as a ligand group, which cannot be discovered with the conventional method based upon the structure similarity of compounds. In other words, it appears that the new model based upon the interaction information can accurately estimate the relationship where a compound with various structures acts on the same protein. Further, compounds, conventionally known as compounds acting on a peptide receptor, such as neuropeptide receptor antagonist, were included in these compounds; however, it was confirmed that they also interact with distantly-related β2AR according to the test.

Example 3

Design of Compound Library

Figure 10:
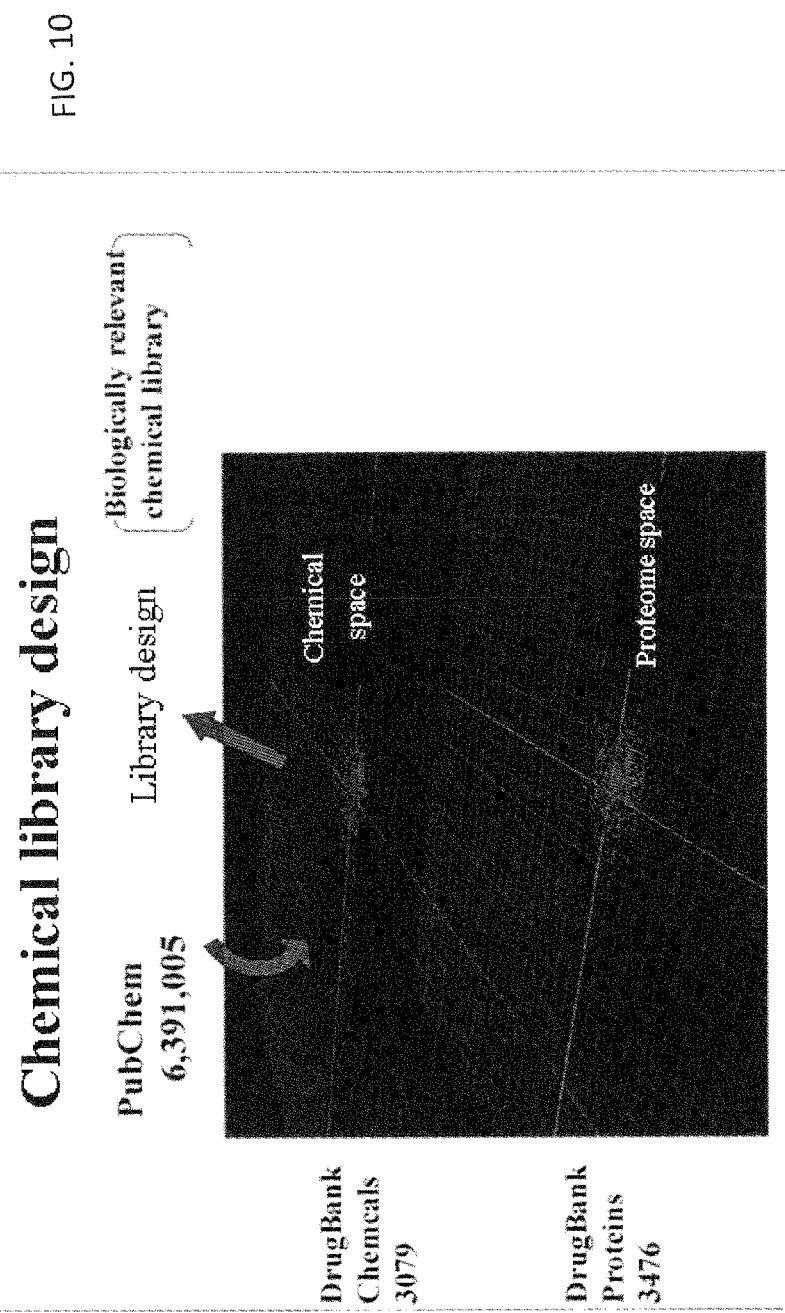
FIG. 10 is a connectional diagram of a compound library design of the present invention.
Figure 13:
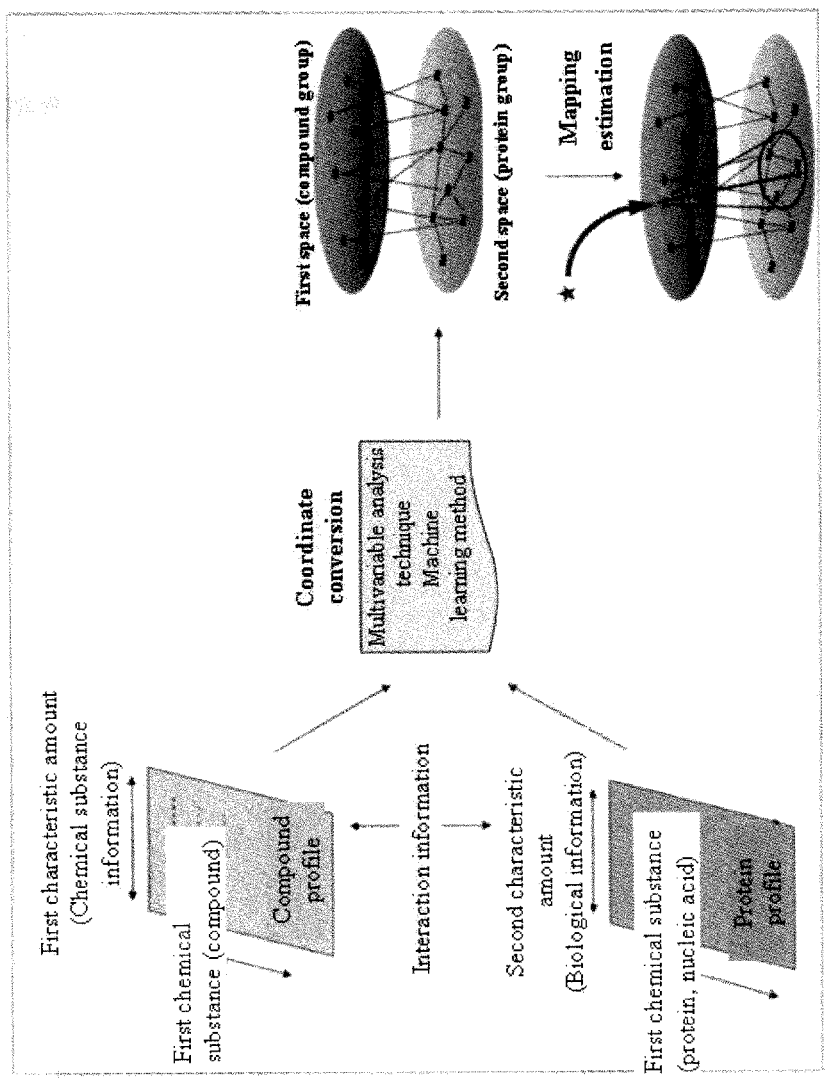
FIG. 13 is a calculation flow on the occasion of applying CCA in the present invention.
Figure 14:
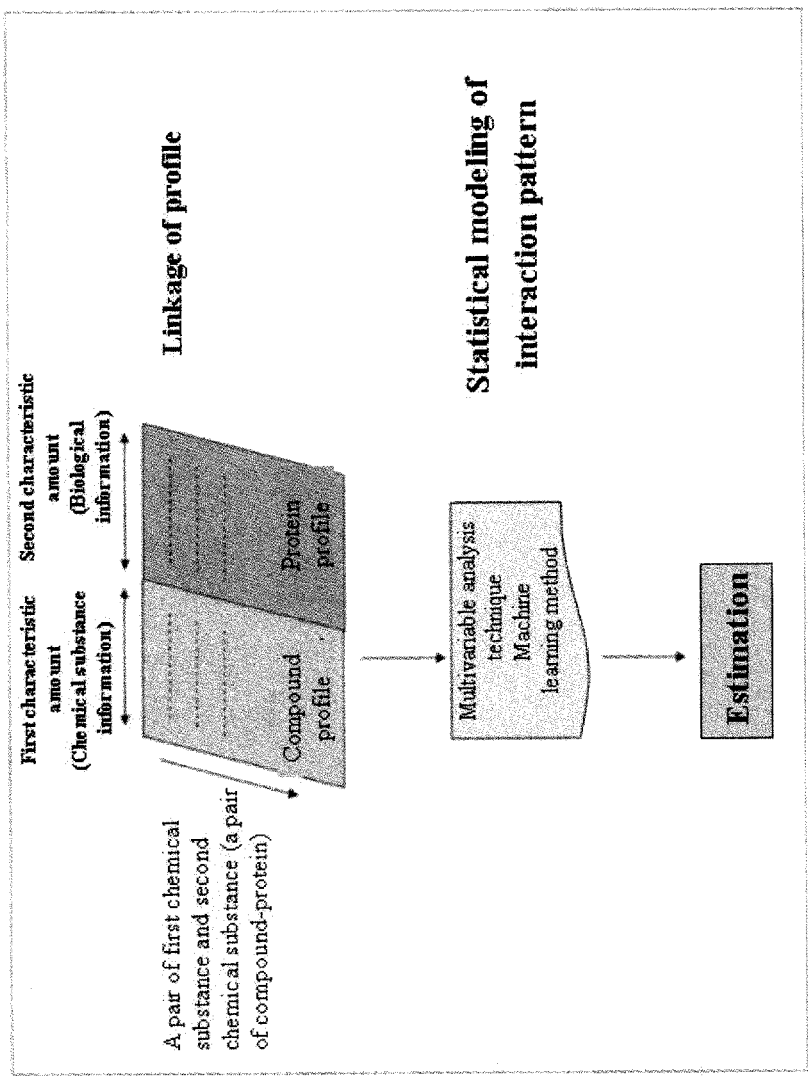
FIG. 14 is a calculation flow on the occasion of applying SVM in the present invention.

A compound library was designed using this technique, i.e., a target gene to a specific compound was estimated. FIG. 10 shows the design technique.

Protein candidates, which can be targeted by these compounds, were estimated using U.S. Pat. No. 6,391,005 compounds within the US NCBI/PubChem database, and a compound library was constructed. Herein, for the preparation of the integrated model between the chemical space and the biological space, which are reference coordinates for estimation, Canada's DrugBank database where data about drugs and target proteins thereof are accumulated was used.

FIG. 11 shows results of bioactivity estimation of PubChem compounds. Each row shows data per score indicating the reliability of binding possibility between a compound and a target protein. In other words, it appears that the higher the score becomes, the higher the reliability of the bioactivity of the compound. It appears that the score herein shows a bindability (statistic significance of binding estimation) between any chemical compound A within the first space and any chemical substance B within the second space.

For example, the binding score between the chemical substance A and the chemical substance B can be defined as follows: It is assumed that the number of all chemical substances within the second space is N, and the number of substances to be bound with the chemical substance A is L. Herein, in the case of considering K chemical substances within the second space adjacent to B, it is assumed that the number to be bound with the chemical substance A is H. On that occasion, the binding score from the chemical substance A to B can be defined as odd score, such as log (H/K)/(L/N)). Inversely, it is assumed that the number of all chemical substances within the second space is n, and the number of substances to be bound with the chemical substance B is l. Herein, in the case of considering k chemical substances within the first space adjacent to A, it is assumed that the number to be bound with the chemical substance B is h. On that occasion, the binding score from the chemical substance B to A can be defined as an odd score, such as log(h/k)/(l/n)). In FIG. 11, the overall score of the binding possibility between the chemical substances A and B were defined as log((H/K)/(L/N))+log((h/k)/(l/n))+20 from the score from the chemical substances A to B and the scores from B to A.

Further, the items in each line indicate the classification per function of the target protein (based upon gene ontology). The numerical values in the table represent the number of (estimated) compounds corresponding to the correspondence portion. For example, protein regarding the receptor activity is targeted, and for compounds showing score value: 27 or more reliability, 198 compounds are estimated.

FIG. 12, as similar to FIG. 11, shows results of bioactivity estimation of PubChem compounds, and the function of the target protein is classified using different references, respectively. The view of FIG. 12 is similar to FIG. 11.

REFERENCES

[1] Okuno Y, Yang J, Taneishi K, Yabuuchi H & Tsujimoto G. GLIDA: GPCR-legend database for chemical genomic drug discovery. *Nucleic Acids Res.* 34, D673-7 (2006).

[2] Fredholm B. B., Fleming W. W., Vanhoutte P. M., & Godfraind T. The role of pharmacology in drug discovery. *Nat. Rev. Drug Discov.* 1, 237-8 (2002)

[3] Wishart D. S., Knox C, Guo A. C., Shrivastava S, Hassanali M, Stothard P, Chang Z & Woolsey J. DrugBank: a comprehensive resources for in silico drug discovery and exploration. *Nucleic Acids Res.* 34 D668-72 (2006)

[4] Roth B. L., Kroeze W. K., Patel S & Lopez E. The multiplicity of Serotonin Receptors: Uselessly Diverse molecules or an embarrassment of riches? *The Neuroscientist* 6,252-252 (2000)

[5] Horn F, Bettler E, Oliveira L, Camp agne F, Cohen F. E. & Vriend G. GPCRDB information system for G protein coupled receptors. Nucleic Acids Res. 31, 294-7 (2003)

[6] Wheeler D. L., Barrett T, Benson D. A., Bryant S. H., Canese K, Chetvernin V, Church D. M., et al. Database resources of the National Center for Biotechnology Information. Nucleic Acids Res. 34, D173-80 (2006)

[7] DRAGON software is available at http://www.talete.mi.it/main_net.htm

[8] Leslie C. S., Eskin E, Cohen A, Weston J & Noble W S. Mismatch string kernels for discriminative Protein classification. Bioinformatics 20, 467-76 (2004)

[9] Vapnik V. N. The Nature of Statistical Learning Theory Springer: New York (1995)

[10] Platt J. Fast Training of Support Vector Machines using Sequential Minimal Optimization; Microsoft Research Technical Report MSRTR-96-14 (1998)

[11] Keerthi S. S., Shevade S. K., Bhattacharyya C & Murthy K. R. K. Improvements to Platt's SMO Algorithm for SVM Classifier Design. Neural Comput. 13, 637-649 (2001)

[12] Chang C. C. & Lin C. J. LIBSVM: a library for support vector machines, Software is Available at http://www.c-sie.ntu.edu.tw/~chkub/libsvm

[13] Platt J. Probabilistic outputs for support vector machines and comparison to regularized likelihood methods. Advances in Large Margin Classifiers (pp. 61-74 (1999)

[14] Oprea T. I Chemical space navigation in lead discovery. Curr. Opin. Chem. Biol. 6, 384-9 (2002)

INDUSTRIAL APPLICABILITY

With this technology, the cost of new drug development is drastically reduced especially in a field of drug discovery, and cycles for research and development can be reduced. With these reductions, a better drug can be launched to markets with a shorter time period compared to the conventional one. Further, the reduction in a ratio of research and development cost occupied in pharmaceutical cost socially enables an expectation of the contribution to a reduction in the burden of medical expenses.

What is claimed is:

1. A computer-based method for estimating a protein-compound interaction of chemical substances, wherein the chemical substances include:
   a first chemical substance, wherein the first chemical substance is a small molecule and comprises a first characteristic amount expressed as a first vector having a compound descriptor calculated from the structure and properties of the first chemical substance, wherein the structure and properties of the first chemical substance are expressed as a plurality of compound descriptors including constitutional descriptors, topological descriptors, walk and path counts, connectivity indices, information indices, 2D autocorrelations, edge adjacency indices, burden eigenvalue descriptors, topological charge indices, eigenvalue-based indices, functional group counts, atom-centered fragments, and molecular properties; and
   a second chemical substance, wherein the second chemical substance is a protein and comprises a second characteristic amount expressed as a second vector having a protein descriptor calculated from only an amino acid sequence of the second chemical substance;
   the method comprising:
      (A) constructing a learning model using a Support Vector Machine algorithm to obtain a hyperplane for performing pattern recognitions of one or more type of information of the first chemical substance and of the second chemical substance, both of which are to be estimated for protein-compound interaction, wherein the first characteristic amount of the first chemical substance having the compound descriptor expressed as the first vector and the second characteristic amount of the second chemical substance having the protein descriptor expressed as the second vector are map- transformed to maximize correlation between chemical space coordinate and biological space coordinate,
      (B) mapping a characteristic vector constructed by combining the first characteristic amount of the first chemical substance to be estimated for interaction and the second characteristic amount of the second chemical substance to be estimated for interaction, into the learning model constructed in step (A) for pattern recognitions, and (C) determining whether or not the first chemical substance to be estimated for interaction interacts with the second chemical substance to be estimated for interaction based on a mapped position of the characteristic vector in step (B) relative to the hyperplane obtained in step (A).

2. The computer-based method for estimation of protein-compound interaction according to claim 1, wherein the determination (C) further comprises:

(C1) calculating a probability score for the interaction of the first chemical substance with the second chemical substance based on the map position of the characteristic vector constructed in step (B) relative to the hyperplane obtained in step (A), and (C2) outputting information regarding the interaction of the first chemical substance and the second chemical substance.

3. A non-transitory computer-readable medium containing programming instructions that cause a computer processor to perform a method for estimation of protein-compound interaction of chemical substances, wherein the chemical substances include:

a first chemical substance, wherein the first chemical substance is a small molecule and comprises a first characteristic amount expressed as a first vector having a compound descriptor calculated from the structure and properties of the first chemical substance, wherein the structure and properties of the first chemical substance are expressed as a plurality of compound descriptors including constitutional descriptors, topological descriptors, walk and path counts, connectivity indices, information indices, 2D autocorrelations, edge adjacency indices, burden eigenvalue descriptors, topological charge indices, eigenvalue-based indices, functional group counts, atom-centered fragments, and molecular properties; and a second chemical substance, wherein the second chemical substance is a protein and comprises a second characteristic amount expressed as a second vector having a protein descriptor calculated from only an amino acid sequence of the second chemical substance;

the method being characterized by comprising:

(A) constructing a learning model using a Support Vector Machine algorithm to obtain a hyperplane for performing pattern recognitions of one or more type of information of the first chemical substance and of the second chemical substance, both of which are to be estimated for protein-compound interaction, wherein the first characteristic amount of the first chemical substance having the compound descriptor expressed as the first vector and the second characteristic amount of the second chemical substance having the protein descriptor expressed as the second vector are map-transformed to maximize correlation between chemical space coordinate and biological space coordinate, (B) mapping a characteristic vector constructed by combining the first characteristic amount of the first chemical substance to be estimated for interaction and the second characteristic amount of the second chemical substance to be estimated for interaction, into the learning model constructed in step (A) for pattern recognitions, and (C) determining whether or not the first chemical substance to be estimated for interaction interacts with the second chemical substance to be estimated for interaction based on a mapped-position of the characteristic vector in step (B) relative to the hyperplane obtained in step (A).

4. The non-transitory computer-readable medium containing programming instructions that cause a computer processor to perform a method for estimation of protein-compound interaction according to claim 3, wherein the determination (C) further comprises:

(C1) calculating a probability score for the interaction of the first chemical substance with the second chemical substance based on the map position of the characteristic vector constructed in step (B) relative to the hyperplane obtained in step (A), and (C2) outputting information regarding the interaction of the first chemical substance and the second chemical substance.

* * * * *